(12) United States Patent
Renkonen et al.

(10) Patent No.: US 6,191,271 B1
(45) Date of Patent: *Feb. 20, 2001

(54) SYNTHETIC DIVALENT SLEX CONTAINING POLYLACTOSAMINES AND METHODS FOR USE

(75) Inventors: Ossi Renkonen, Espoo; Risto Renkonen, Westendinkuja, both of (FI)

(73) Assignee: Glycim Oy, Espoo (FI)

(*) Notice: Under 35 U.S.C. 154(b), the term of this patent shall be extended for 0 days.

This patent is subject to a terminal disclaimer.

(21) Appl. No.: 09/148,076

(22) Filed: Sep. 4, 1998

Related U.S. Application Data

(60) Provisional application No. 60/057,660, filed on Sep. 5, 1997.

(51) Int. Cl.[7] .............................. C08B 37/00; C12P 19/04

(52) U.S. Cl. ........................... 536/123; 536/55; 536/55.1; 536/55.2; 435/84; 435/97; 435/101; 514/54

(58) Field of Search ................................ 435/84, 97, 101; 536/55, 55.1, 55.2, 123; 514/54

(56) References Cited

U.S. PATENT DOCUMENTS

| | | | |
|---|---|---|---|
| 5,352,670 | 10/1994 | Venot et al. | 514/54 |
| 5,374,541 | 12/1994 | Wong et al. | 435/74 |
| 5,409,817 | 4/1995 | Ito et al. | 435/74 |
| 5,426,178 | 6/1995 | Laine et al. | 536/1.11 |
| 5,559,103 | 9/1996 | Gaeta et al. | 514/56 |
| 5,965,544 | 10/1999 | Renkonen et al. | 514/54 |

FOREIGN PATENT DOCUMENTS

| | | |
|---|---|---|
| 0 319 253 | 6/1989 | (EP) . |
| 0 577 580 | 1/1994 | (EP) . |
| 0 627 442 | 12/1994 | (EP) . |
| WO 91/19501 | 12/1991 | (WO) . |
| WO 91/19502 | 12/1991 | (WO) . |
| WO 92/02527 | 2/1992 | (WO) . |
| WO 92/22565 | 12/1992 | (WO) . |
| WO 94/26760 | 11/1994 | (WO) . |
| WO 95/01361 | 1/1995 | (WO) . |
| WO 95/03059 | 2/1995 | (WO) . |
| WO 95/06057 | 3/1995 | (WO) . |
| WO 95/29681 | 11/1995 | (WO) . |
| WO 97/12892 | * 4/1997 | (WO) . |

OTHER PUBLICATIONS

Arbonés, M. L. et al., "Lymphocyte Homing and Leukocyte Rolling and Migration Are Impaired in L–Selectin–Deficient Mice," *Immunity* 1(4):247–260 (1994).

Baumhueter, S. et al., "Binding of L–Selectin to the Vascular Sialomucin CD34," *Science* 262:436–438 (1993).

Bertozzi, C. R., "Cracking the carbohydrate code for selectin recognition," *Chem. and Biol.* 2(11):703–708 (1995).

Buerke, M. et al., "Sialyl Lewis[x]–containing Oligosaccharide Attenuates Myocardial Reperfusion Injury in Cats," *J. Clin. Invest.* 93(3):1140–1148 (1994).

Crottet, P. et al., "Subsets of sialylated, sulfated mucins of diverse origins are recognized by L–selectin. Lack of evidence for unique oligosaccharide sequences mediating binding," *Glycobiol.* 6(2):191–208 (1996).

DeFrees, S. A. et al., "Ligand Recognition by E–Selectin: Analysis of Conformation and Activity of Synthetic Monomeric and Bivalent Sialyl Lewis X Analogs," *J. Am. Chem. Soc.* 115(16):7549–7550 (1993).

DeFrees, S. A. et al., "Ligand Recognition by E–Selectin: Synthesis, Inhibitory Activity, and Conformational Analysis of Bivalent Sialyl Lewis x Analogs," *J. Am. Chem. Soc.* 117(1):66–79 (1995).

de Vries, T. et al., "Efficient enzymatic synthesis of the sialyl–Lewis[x] tetrasaccharide: A ligand for selectin–type adhesion molecules," *FEBS Letters* 330(3):243–248 (1993).

Hemmerich, S. et al., "Structure of the O–Glycans in Gly–CAM–1, an Endothelial–derived Ligand for L–selectin," *J. Biol. Chem.* 270(20):12035–12047 (1995).

Hirota, K. et al., "Highly expressed human sialyl Lewis[x] antigen on cell surface of *Streptococcus gallolyticus*," *The Lancet* 347(9003):760 (1996).

Hughes, S., "Carbohydrate research—a new source of therapeutics," *Scrip Magazine* 28–31 (1994).

Ichikawa, Y. et al., "Chemical–Enzymatic Synthesis and Conformational Analysis of Sialyl Lewis x and Derivatives," *J. Am. Chem. Soc.* 114(24):9283–9298 (1992).

Kashem, M. A. et al., "Chemoenzymic synthesis of sialylated and fucosylated oligosaccharides having an N–acetyllactosaminyl core," *Carbohydrate Research* 250(1):129–144 (1993).

Lasky, L. A., "Selectin–Carbohydrate Interactions and the Initiation of the Inflammatory Response," *Ann. Rev. Biochem.* 64:113–139 (1995).

Lefer, D. J. et al., "A Novel Sialyl Lewis[x] Analog Attenuates Neutrophil Accumulation and Myocardial Necrosis After Ischemia and Reperfusion," *Circulation* 90(5):2390–2401 (1994).

Leppänen, A. et al., "Human Serum Contains a Novel β1,6–N–Acetylglucosaminyltransferase Activity That Is Involved in Midchain Branching of Oligo(N–acetyllactosaminoglycans)," *Biochemistry* 30(38):9287–9296 (1991).

(List continued on next page.)

Primary Examiner—Francisco Prats
(74) Attorney, Agent, or Firm—Sterne, Kessler, Goldstein & Fox P.L.L.C.

(57) ABSTRACT

The present invention is directed to novel compositions and their use in the treatment of inflammatory responses. Specifically, the invention is directed to novel synthetic oligosaccharide constructs and their use to block lymphocyte binding to correspondent oligosaccharides on the endothelial surface, and thus reduce or otherwise ameliorate an undesired inflammatory response. The invention is further directed to the use of such constructs in other disease states characterized by selectin binding, such as bacterial infections and metastatic cancers.

7 Claims, 13 Drawing Sheets

OTHER PUBLICATIONS

Leppänen, A. et al., "In Vitro Biosynthesis of a Decasaccharide Prototype of Multiply Branched Polylactosaminoglycan Backbones," *Biochemistry* 36(23):7026–7036 (Jun. 1997).

Litscher, E. S. et al., "Oligosaccharide Constructs with Defined Structures That Inhibit Binding of Mouse Sperm to Unfertilized Eggs in Vitro," *Biochem.* 34(14):4662–4669 (1995).

Lowe, J. B. et al., "Molecular Cloning of a Human Fucosyltransferase Gene That Determines Expression of the Lewis x and VIM–2 Epitopes but Not ELAM–1–dependent Cell Adhesion," *J. Biol. Chem.* 266(26):17467–17477 (1991).

Maaheimo, H. et al., "Synthesis of a divalent sialyl Lewis x O–glycan, a potent inhibitor of lymphocyte–endothelium adhesion: Evidence that multivalency enhances the saccharide binding to L–selectin," *Eur. J. Biochem.* 234(2):616–625 (1995).

Maaheimo, H. et al., "$^1$ and $^{13}$C NMR analysis of the pentasaccharide Galβ(1→4)GlcNAcβ(1→3)-[GlcNAcβ(1→6)]Galβ(1→4)GlcNAc synthesized by the mid–chain β–(1→6)–D–N–acetylglucosaminyltransferase of rat serum," *Carbohydrate Research* 297(2):145–151 (Jan. 1997).

Maaheimo, H. et al., "Enzyme–aided construction of medium–sized alditols of complete O–linked saccharides: The constructed hexasaccharide alditol Galβ1–4GlcNAcβ1–6Galβ1–4GlcNAcβ1–6(Galβ1–3)GalNAc–ol resists the action of endo–β–galactosidase from *Bacteroides fragilis*," *FEBS Letters* 349(1):55–59 (1994).

Maemura, K., and Fukuda, M., "Poly–N–acetyllactosaminyl O–Glycans Attached to Leukosialin," *J. Biol. Chem.* 267(34):24379–24386 (1992).

Majuri, M.–L. et al., "Expression and Function of α2,3–Sialyl– and α1,3/1,4–Fucosyltransferases in Colon Adenocarcinoma Cell Lines: Role in Synthesis of E–Selectin Counter–Receptors," *Int. J. Cancer* 63(4):551–559 (1995).

Majuri, M.–L. et al., "Recombinant E–selectin–protein mediates tumor cell adhesion via sialyl–Lea and sialyl–Lex," *Biochem. Biophys. Res. Comm.* 182(3):1376–1382 (1992).

Malhotra, R. et al., "Anionic phospholipids bind to L–selectin (but not E–selectin) at a site distinct from the carbohydrate–binding site," *Biochem J.* 314(1):297–303 (1996).

Mulligan, M. S. et al., "Protective effects of oligosaccharides in P–selectin–dependent lung injury," *Nature* 364(6433):149–151 (1993).

Natsuka, S. et al., "Molecular Cloning of a cDNA Encoding a Novel Human Leukocyte α–1,3–Fucosyltransferase Capable of Synthesizing the Sialyl Lewis x Determinant," *J. Biol. Chem.* 269(24):16789–16794 (1994).

Natunen, J. et al., "Enzymatic synthesis of two lacto–N–neohexaose–related Lewis x heptasaccharides and their separation by chromatography on immobilized wheat germ agglutinin," *Glyobiol.* 4(5):577–583 (1994).

Niemelä, R. et al., "α1,3–Fucosylation of branched blood group I–type oligo–(N–acetyllactosamino) glycans by human milk transferases is restricted to distal N–acetyllactosamine units: The resulting isomers are separated by WGA–agarose chromatography," *Glycoconjugate J.* 12(1):36–44 (1995).

Niemelä, R. et al., "Enzyme–assisted synthesis of a bivalent high–affinity dodecasaccharide inhibitor of mouse gamete adhesion—The length of the chains carrying distal α1,3–bonded galactose residues is critical," *FEBS Letters* 367(1):67–72 (1995).

Niemelä, R. et al., "Site–directed enzymatic α–(1→3)–L–fucosylation of the tetrasaccharide Galβ(1→4)GlcNAcβ(1→3)Galβ(1→4)GlcNAc at the distal N–acetyllactosamine unit," *Carbohydrate Research* 279:331–338 (1995).

Norgard, K. E. et al., "Characterization of a Specific Ligand for P–selectin on Myeloid Cells: A Minor Glycoprotein with Sialylated O–linked Oligosaccharides," *J. Biol. Chem.* 268(17):12764–12774 (1993).

Paavonen, T. et al., "Selective Expression of Sialyl–Lewis X and Lewis A Epitopes, Putative Ligands for L–selectin, on Peripheral Lymph–node High Endothelial Venules," *Am. J. Pathol.* 141(6):1259–1264 (1992).

Patel, T. P. et al., "Isolation and Characterization of Natural Protein–Associated Carbohydrate Ligands for E–Selectin," *Biochemistry* 33(49):14815–14824 (1994).

Powell, L. D. et al., "Characterization of Sialyloligosaccharide Binding by Recombinant Soluble and Native Cell–associated CD22: Evidence for a Minimal Structural Recognition Motif and the Potential Importance of Multisite Binding," *J. Biol. Chem.* 270(13):7523–7532 (1995).

Renkonen, O. et al., "*Escherichia coli* β–galactosidase unexpectedly cleaves the hexasaccharide Galβ1–4GlcNAcβ1–3(Galβ1–4GlcNAcβ1–6)Galβ1–4GlcNAc without branch specificity," *Biochem Cell Biol.* 68(7–8):1032–1036 (1990).

Renkonen, O. et al., "The Linear Tetrasaccharide, Galβ1–4GlcNacβ1–6Galβ1–4GlcNAc, Isolated from Radiolabeled Teratocarcinoma Poly–N–acetyllactosaminoglycan Resists the Action of *E. freundii* Endo–β–galactosidase," *Glycoconjugate J.* 6(1):129–140 (1989).

Renkonen, R. et al., "Characterization of High Endothelial–like Properties of Peritubular Capillary Endothelium During Acute Renal Allograft Rejection," *Am. J. Pathol.* 137(3):643–651 (1990).

Renouf, D. V. et al., "Conformational studies of the backbone (poly–N–acetyllactosamine) and the core region sequences of O–linked carbohydrate chains," *Int. J. Biol. Macromol.* 15(1):37–42 (1993).

Seppo, A. et al., "Synthesis of a tetravalent sialyl Lewis x glycan, a high–affinity inhibitor of L–selectin–mediated lymphocyte binding to endothelium," *Glycobiol.* 6(1):65–71 (1996).

Seppo, A. et al., "Enzymatic Synthesis of Octadecameric Saccharides of Multiply Branched Blood Group I–Type, Carrying Four Distal α1,3–Galactose or β1,3–GlcNAc Residues," *Biochem.* 34(14):4655–4661 (1995).

Seppo, A. et al., "Wheat germ agglutinin chromatography of GlcNAcβ1–3(GlcNAcβ1–6)Gal and GlcNAcβ1–3(GlcNAcβ1–6)Galβ1–4GlcNAc, obtained by in vitro synthesis and by partial cleavage of teratocarcinoma poly–N–acetyllactosaminoglycans," *Biochem. Cell Biol.* 68(1):44–53 (1990).

Stroud, M. R. et al., "Monosialogangliosides of Human Myelogenous Leukemia HL60 Cells and Normal Human Leukocytes. 2. Characterization of E–Selectin Binding Fractions, and Structural Requirements for Physiological Binding to E–Selectin," *Biochemistry* 35(3):770–778 (1996).

Tedder, T. F. et al., "The selectins: vascular adhesion molecules," *FASEB J.* 9(10):866–873 (1995).

Toppila, S. et al., "L–selectin ligands in rat high endothelium: multivalent sialyl Lewis x glycans are high–affinity inhibitors of lymphocyte adhesion," *Eur. J. Immunol.* 27(6):1360–1365 (Jun. 1997).

Turunen, J. P. et al., "De Novo Expression of Endothelial Sialyl Lewis$^a$ and Sialyl Lewis$^x$ during Cardiac Transplant Rejection: Superior Capacity of a Tetravalent Sialyl Lewis$^x$ Oligosaccharide in Inhibiting L–Selectin–dependent Lymphocyte Adhesion," *J. Exp. Med.* 182(4):1133–1141 (1995).

Turunen, J. P. et al., "Sialyl Lewis$^x$– and L–selectin–dependent site–specific lymphocyte extravasation into renal transplants during acute rejection," *Eur. J. Immunol.* 24(5):1130–1136 (May 1994).

Turunen, J. P. et al., "Evidence That Lymphocyte Traffic into Rejecting Cardiac Allografts Is CD11a– and CD49d–Dependent," *Transplantation* 54(6):1053–1058 (1992).

Vilkman, A. et al., "Elongation of both branches of biantennary backbones of oligo–(N–acetyllactosamino)glycans by human serum (1→3)–N–acetyl–β–D–glucosaminyltransferase," *Carbohydrate Res.* 226(1):155–174 (1992).

Welply, J. K. et al., "Multivalent sialyl–LeX: potent inhibitors of E–selectin–mediated cell adhesion; reagent for staining activated endothelial cells," *Glycobiol.* 4(3):259–265 (1994).

Wilkins, P. P. et al., "Structures of the O–Glycans on P–selectin Glycoprotein Ligand–1 from HL–60 Cells," *J. Biol. Chem.* 271(31):18732–18742 (1996).

English language abstract of WO 95/01361 (Document AO2), Dialog File 351, WPI Acc. No.: 95–060942/08 (1995).

English language abstract of WO 95/06057 (Document AP2), Dialog File 351, WPI Acc. No.: 95–115200/15 (1995).

\* cited by examiner

SYNTHETIC DIVALENT SLEX CONTAINING POLYLACTOSAMINES AND METHODS FOR USE

CROSS-REFERENCE TO RELATED APPLICATION

This application claims the benefit of earlier filed U.S. provisional patent application no. 60/057,660, filed Sep. 5, 1997.

FIELD OF THE INVENTION

The present invention is directed to novel compositions and their use in the treatment of inflammatory responses. Specifically, the invention is directed to novel synthetic oligosaccharide constructs, especially divalent sLex decorated poly-N-acetyllactosamines and their use to block lymphocyte binding to correspondent oligosaccharides on the endothelial surface, and thus reduce or otherwise ameliorate an undesired inflammatory response and other disease states characterized by lymphocyte binding. Furthermore the invention is directed to the use of the novel saccharides to block bacterial adherence to endothelium and thus prevent and/or treat bacterial infections. A further use of the present invention lies in the field of cancer treatment where metastasis of sLex-positive tumor cells is inhibited by these glycans.

BACKGROUND OF THE INVENTION

Selectin Mediated Cell Adhesion

The migration of white blood cells from the blood to regions of pathogenic exposure in the body is called the inflammatory cascade. Cell adhesion events allow for specific binding of a leukocyte to the endothelium of the vessel that is adjacent to the inflammatory insult; such adhesion events counteract the high vascular shear forces and high blood flow rates that tend to keep the leukocyte circulating, and help guide the leukocyte to the required site.

Four families of vascular adhesion molecules are involved in the migration of leukocytes during the inflammatory response: (1) the integrin family, (2) the counterreceptors of the integrin family, the immunoglobulin superfamily, (3) the selectin family, and (4) the counterreceptors of the selectin family, specialized carbohydrates displayed by the sialomucin adhesion family.

Selectins are also known as "lectin cell adhesion molecules" (LEC-CAMs). Selectins are classified into three groups: L-selectin (LECAM-1, LAM-1, $gp90^{MEL}$, Leu-8, TQ-1, CD62L and DREG) is expressed on various leukocytes, and is constitutively expressed on lymphocytes, monocytes, neutrophils, and eosinophils. E-selectin (LECAM-2, CD62E and ELAM-1) is expressed on endothelium activated by inflammatory mediators. P-selectin (GMP-140, PADGEM, LECAM-3 and CD62P) is stored in alpha granules of platelets and Weibel-Palade bodies of endothelial cells and is also expressed on endothelium activated by inflammatory stimuli. All members of the selectin family appear to mediate cell adhesion through the recognition of carbohydrates.

The current concept of leukocyte extravasation is based on the consecutive action of several adhesion molecules located on the surface of leukocytes and the endothelium. Lymphocyte extravasation is initiated by the interaction of members of the selectin family and their oligosaccharide-containing counterreceptors. For a review of the current knowledge on lymphocyte adhesion, see e.g., Springer, T. A., Annu. Rev. Physiol. 57:827–872 (1995).

All selectins bind to sialyl Lewis x (NeuNAcα2-3Galβ1-4(Fucα1-3)GlcNAc) (sLe$^x$ or sLex) and sialyl Lewis a (NeuNAcα2-3Galβ1-3(Fucα1-4)GlcNAc) (sLe$^a$ or sLea) as well as related carbohydrate sequences (Bertozzi, C., Chemistry and Biology, 2:703–708 (1995)). L-selectin-dependent recognition precedes normal lymphocyte extravasation into peripheral lymph nodes (Gallatin, W. M. et al., Nature 303:30–34 (1983)) and into sites of inflammation (Ley, K. et al., Blood 77:2553–2555 (1991)), both of which are impaired in L-selectin deficient mice (Arbones, M. L. et al., Immunity 1:247–260 (1994)).

Several glycoproteins have been shown to act as counterreceptors for L-selectin. A common denominator for the cloned ligands GlyCAM-1, CD34, MAdCAM-1 and PSGL-1 (Baumhueter, S. et al., Science, 262:436–438 (1993); Briskin, M. J. et al., Nature, 363:461–464 (1993); Lasky, L. A. et al., Cell 69:927–938 (1992); Walcheck, B. et al., J. Clinical Investigation 98:1081–1087 (1996)), is the mucin type protein core rich of 0-linked glycan decorations which are crucial for the selectin recognition. The glycosylation of GlyCAM-1 and PSGL-1 has been characterized in greater detail, among other saccharides these proteins have been shown to carry sulfated sLex and sLexLexLex epitopes, respectively (Hemmerich, S. et al., J. Biol. Chem. 270:12035–12047 (1995); Wilkins, P. P. et al., J. Biol. Chem. 271:18732–18742 (1996)).

High endothelial cells in peripheral lymph nodes express sialyl Lewis a and sialyl Lewis x (sLea and sLex) epitopes (Paavonen and Renkonen, Am. J. Pathol. 141:1259–1264 (1992); Munro, J. M. et al., Am. J. Pathol. 141:1397–1408 (1992); Sawada, M. et al., Biochem. Biophys. Res. Comm. 193:337–347 (1993)) which are parts ofthe L-selectin counterreceptor. The endothelial cells in several other locations are sLea and sLex negative, but inflammatory stimuli can induce previously negative endothelium to express these oligosaccharide structures de novo (Turunen, J. et al., Eur. J. Immunol. 24:1130–1136 (1994)). It has been shown that cultured endothelial cells possess the machinery to generate at least sLex, since they have several functional α2,3 sialyl- and α1,3 fucosyltransferases, enzymes involved in generating sLex from (poly)lactosamines (Majuri, M. et al., Eur. J. Immunol. 24:3205–3210 (1994)).

A number of studies have proposed that selectins are involved in a wide variety of acute and chronic inflammatory conditions in many tissues.

Being essential to the early phases of leukocyte extravasation cascade, the interactions of selectins and their sLex-containing counterreceptors offer an attractive site for anti-inflammatory interventions (Ley, K. and Tedder, T., J. Immunol. 155:525–528 (1995); Springer, T. A., Annu Rev. Physiol 57:827–872 (1995); Tedder, T., et al, FASEB Journal 9:866–73 (1995)). Monovalent sLex glycans have been shown to inhibit L-selectin mediated lymphocyte binding in vitro (Turunen, J. et al., Eur. J. Immunol. 24:1130–1136 (1994)), and they also inhibit PMN extravasation in animal models of acute inflammation and reperfusion injury (Lefer, D. J. et al., Circulation 90:2390–401 (1994)).

Polylactosamines carrying single epitopes of sLexLex- and sLexLexLex-type appear to be recognized by E- and P-selectins with higher affinity than analogous oligosaccharides bearing single sLex-units (Patel, T. P. et al., Biochemistry 33:14815–24 (1994); Stroud, M. R. et al., Biochemistry 35:770–778 (1996); Wilkins, P. P. et al., J. Biol. Chem. 271:18732–18742 (1996)).

U.S. Pat. No. 5,352,670 to Venot et al. discloses a method for the enzymatic synthesis of an α-sialylated oligosaccharide glycoside using sialyltransferase, a CMP-sialic acid analogue as the sialic acid donor and an oligosaccharide glycoside acceptor molecule, having a βGal(1-3)βGlcNAc or βGal(1-4)βGlcNAc disaccharide on the nonreducing terminus.

International Patent Publication No. WO 95/03059 (Gaeta et al.) discloses a synthetic saccharide that contains two glycosidically linked sLex moieties, that are useful in blocking cellular adhesion, especially by inhibiting E-selectin binding. These sLex containing oligosaccharides are synthesized on a galactose backbone.

International Patent Publication No. WO 97/12892 (Renkonen, O. and Renkonen, R.) discloses synthetic multivalent sLex containing polylactosamines and their use to block lymphocyte binding to correspondent oligosaccharides on the endothelial surface.

SUMMARY OF THE INVENTION

The recognition of cell surface L-selectin by its carbohydrate ligands causes lymphocytes to roll on capillary endothelium at sites of inflammation. As this primary contact is a prerequisite for extravasation of the leukocytes to the tissue, its inhibition by free oligosaccharides capable of competing with the natural L-selectin ligands is an attractive therapeutic option.

Recognizing the importance of controlling abnormal inflammatory conditions, and cognizant of the need for drugs to mediate the same, the inventors synthesized oligosaccharides that are capable of inhibiting selectin-mediated responses. These studies culminated in the identification of novel oligosaccharides that block the lymphocyte L-selectin from binding to correspondent oligosaccharides on the endothelial surface and in clinical treatments designed to reduce inflammation as a result of administration of such oligosaccharides in a patient in need of such treatment.

Accordingly, the invention is first directed to synthetic oligosaccharides, especially divalent sLex containing oligosaccharides, essentially free of natural contaminants, and compositions containing the same. The synthetic oligosaccharides of the present invention comprise a polylactosamine backbone $(LN)_n$ where $n \geq 5$ and the interresidual links are β1-3' and/or β1-6', interlinked to similar biantennary arrays having two extended branches that are α2,3-sialylated and α1,3-fucosylated at the chain termini. Such oligosaccharides are shown to be capable of binding selectin molecules that are on the outer surface of lymphocytes, especially L-selectin, thereby preventing the lymphocytes from binding to selectin correspondent oligosaccharides on the endothelial surface.

The invention is further directed to the divalent sialyl-LexLN and sialyl-diLex polylactosamines. The divalent sialyl-diLex glycan is a powerful antagonist for L-selectin having an $IC_{50}$ of 50 nM at lymph node endothelium, and inhibiting L-selectin dependent lymphocyte adhesion to capillaries of rejecting rat heart allografts even more efficiently ($IC_{50}$=5 nm). It reduces extravasation of lymphocytes at sites of inflammation without severely endangering the normal recirculation of lymphocytes via lymph nodes.

The invention is further directed to the divalent sialyl-LexLNLN, sialyl-diLexLN and sialyl-triLex polylactosamines. The divalent sialyl-triLex glycan is a powerful inhibitor of L-selectin-mediated cell adhesion.

The invention is also directed to a method of enzymatically synthesizing such oligosaccharides.

The invention is further directed to a method for inhibiting lymphocyte selectin-mediated binding to endothelial surfaces, especially L-selectin-mediated binding, but also E- and P- selectin binding, by the administration of the oligosaccharide compositions of the invention, especially where such lymphocyte-endothelial cell adhesion reaction is associated with chronic or acute inflammation that is the result of transplantation rejection, arthritis, rheumatoid arthritis, infection, dermatosis, inflammatory bowel disease, and autoimmune disease.

The invention is further directed to a method for preventing and/or treating bacterial infections by the administration of the oligosaccharide compositions of the invention.

The invention is further directed to a method for treating cancer by the administration of the oligosaccharide compositions of the invention.

The invention is further directed to a method for blocking or impeding the deleterious migration of leukocytes to the site of pathogenic exposure in any inflammatory condition.

DETAILED DESCRIPTION OF THE PREFERRED EMBODIMENTS

The present invention relates to novel synthetic oligosaccharides and pharmaceutically acceptable compositions containing the same, and to their use in a therapeutic method for the treatment of acute or chronic inflammatory conditions. The synthetic oligosaccharides of the present invention comprise a polylactosamine backbone (LN)$_n$ where n≧5 and the interresidual links are β1-3' and/or β1-6', interlinked to similar biantennary arrays having two extended branches that are α2,3-sialylated and α1,3-fucosylated at the chain termini.

Figure 1:
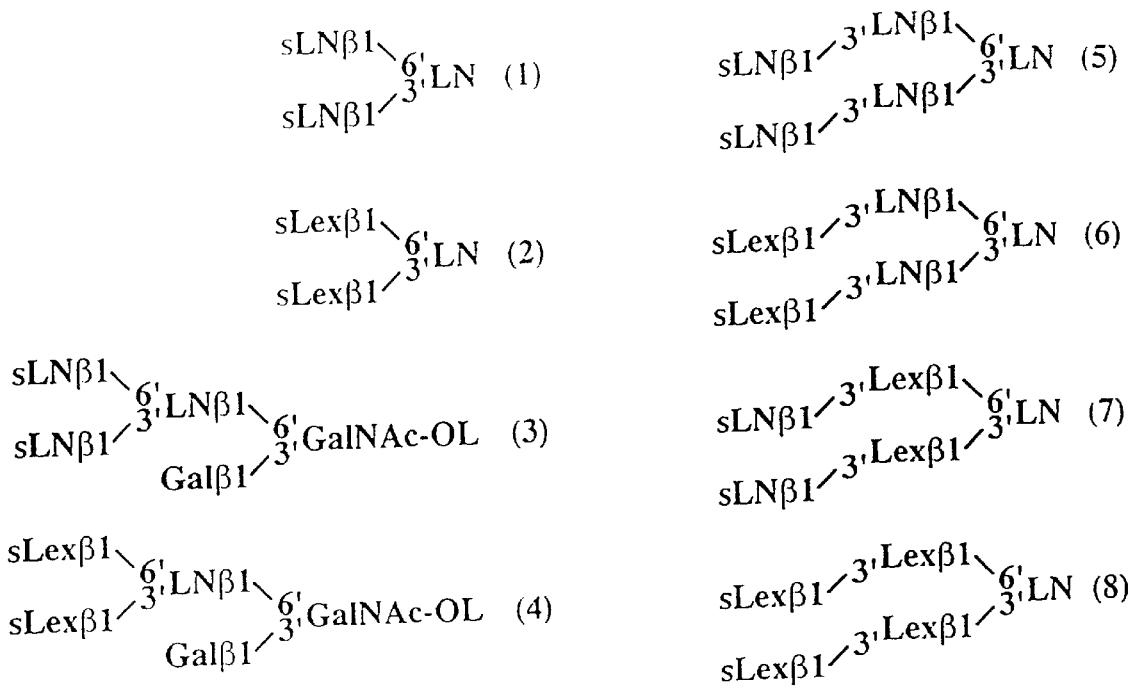
FIG. 1. Structures of the enzymatically synthesized oligosaccharides.

Such oligosaccharides are preferably divalent multimers of sLex as diagramed in FIG. 1. In one preferred embodiment, the synthetic oligosaccharide is the divalent sLexLN- or sdiLex-saccharide as shown in FIG. 1. In another preferred embodiment, the synthetic oligosaccharide is a divalent sLexLNLN-,sLexLexLN-, or striLex-saccharide. Synthesis of the oligosaccharides of the invention is achieved by chemical and/or enzymatic means. For example, the construction of divalent sLexLN-hexasaccharide can be achieved by introducing to the decasaccharide LNβ1,3'LNβ1,3'(LNβ1,3'LNβ1,6')LN (Niemela, R. et al., FEBS Lett. 367:67–72 (1995)) a "protective" β1,6-bonded branch to the inner galactose on both the 3' and 6'-bonded branches by using the mid-chain β1,6N-acetylglucosyltransferase activity present in rat serum. The resulting purified dodecasaccharide is first α2,3 sialylated by treating with CMP-NeuNAc and α2,3 sialyltransferase from human placenta andthen α1,3fucosylated with GDP-fucose and partially purified α1,3/4 fucosyltransferase from human milk. The product is further treated with β-N-acetylhexosaminidase to remove the protective GlcNAc residues. (Also see Example 2). The divalent sLexLex-heptasaccharide can be achieved from SAα2,3'LNβ1,3'LNβ1,3'(SAα2,3'LNβ1,3'LNβ1,6')LN by exhaustively α1,3 fucosylating with GDP-fucose and partially purified α1,3/4 fucosyltransferase from human milk. The characterization of the constructs was carried out by $^1$H NMR-spectroscopy at 500 MHz. (Also see Example 2).

In the present invention, the crucial role of the terminal sLex-epitopes in the recognition of L-selectin is emphasized. Further, it is shown that the additional inner Lex-residues enhance the affinity of the ligands.

In the method of treating inflammation of the invention, the patient (animal and especially human) in need of such treatment is administered efficacious levels of the synthetic carbohydrate of the invention, generally in a pharmaceutically acceptable composition. The patient may also be administered compositions containing mixtures ofthe synthetic carbohydrates ofthe invention, especially efficacious mixtures of the divalent sLexLN and sLexLex compounds shown in FIG. 1, and the divalent sLexLNLN, sLexLexLN and sLexLexLex compounds. Such pharmaceutical compositions may further contain other desired ingredients, such as, for example, antibodies or conjugates thereofthat recognize and bind to leukocyte L-selectin, so as to act in concert with and enhance the efficacious ability of the synthetic carbohydrates of the invention.

By "inflammatory condition" is meant a physiological or pathological condition which is accompanied by an inflammatory response. Such conditions include, but are not limited to the various organ/tissue transplants such as skin grafts, kidney, heart, lung, liver, bone marrow, cornea, pancreas, small bowel, organ/tissue rejection, arthritis, an infection, a dermatose, inflammatory bowel disease and autoimmune diseases.

By "essentially free of contaminants" is meant that the multivalent sLex is purified to a degree such that the product contains no, or acceptable levels of, undesired or unnecessary substances that had been present during the in vitro or in vivo synthesis of said divalent sLex.

The term "treatment" or "treating" is intended to include the administration of the synthetic oligosaccharides of the invention to a subject for purposes which may include prophylaxis, amelioration, prevention or cure of disorders mediated by selectin adhesion events, especially L-selectin-mediated adhesion events. Such treatment need not necessarily completely ameliorate the inflammatory response. Further, such treatment may be used in conjunction with other traditional treatments for reducing the inflammatory condition known to those of skill in the art.

The methods of the invention may be provided as a "preventive" treatment before detection of, for example, an inflammatory state, so as to prevent the same from developing in patients at high risk for the same, such as, for example, transplant patients.

When administered to a human or animal patient, the composition of the invention may be formulated in any manner which makes it suitable for oral, parenteral, including intravenously, intramuscularly, or subcutaneously, intracistemal, intravaginal, intraperitoneal, local, including powders, ointments, or drops, nasal, including sprays, topical, enteric or rectal administration. Thus, the reagent may be in the form of, for instance, an injectable formulation, aerosol formulation, suspension, solution, dispersion, emulsion, sterile powder, enema, etc. The reagent may be formulated with pharmaceutically acceptable excipients, carriers, solvents, or vehicles, e.g., isotonic saline, ethanol, polyol, polyethylene glycol, glycerol and the like, in accordance with conventional pharmaceutical practice. The dosage level of the reagent will be sufficient to provide an anti-inflammatory effect by the blocking of selectin, and especially L-selectin-mediated adhesion events in the patient.

Solid dosage forms for oral administration include capsules, tablets, pills, powders, and granules. In such solid dosage forms, the active compound may be admixed with at least one inert customary excipient, filler or extender, binder, humectant, disintegrating agent, solution retarder, wetting agent, adsorbent, lubricant, and/or buffering agent. Solid dosage forms such as tablets, dragees, capsules, pills, and granules can be prepared with coatings and shells. The active compounds can also be in microencapsulated form with one or more excipients.

Liquid dosage forms for oral administration include pharmaceutically acceptable emulsions, solutions, suspensions, syrups and elixers. In addition to the active compounds, the liquid dosage forms may contain inert diluents commonly used in the art such as water or other solvents, solubilizing agents and emulsifiers.

Besides such inert diluents, the composition can also include adjuvants, such as wetting agents, emulsifying and suspending agents, sweetening, flavoring and perfuming agents.

Suspensions, in addition to the active compounds, may contain suspending agents.

The compositions of this invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any nontoxic, physiologically acceptable, and metabolizable lipid capable of forming liposomes can be used. The present compositions in liposome form can contain, in addition to the synthetic divalent sLex containing polylactosamines of the invention, stabilizers, preservatives, excipients, and the like. The preferred lipids are the phospholipids, and the phosphatidyl cholines (lecithins), both natural and synthetic. Methods of forming liposomes are well known in the art.

The compositions and methods of the invention are suitable for treating any condition involving a selectin, and especially an L-selectin-mediated adhesion increased inflammatory reaction. Thus, the reagent is useful for treating conditions including but not limited to septic shock, chronic inflammatory diseases such as psoriasis, and rheumatoid arthritis and reperfusion injury that occurs following heart attacks, strokes and organ transplants, traumatic shock, multiorgan failure, autoimmune diseases, asthma, inflammatory bowel disease, tissue rejection, arthritis, an infection, especially local infections, dermatoses, etc. In each case, an effective amount of the compounds of the present invention is administered either alone or as a part of a pharmaceutically acceptable composition to a patient in need of such treatment. It is also recognized that a combination of the compounds may be administered to a patient in need of such administration.

Cell adhesion involving sLex and sLea has been shown to play a role in the metastasis of certain cancers. Accordingly, a further use of the present invention is in cancer treatment where metastasis of sLex positive tumor cells can be inhibited by these glycans.

In another embodiment, efficacious levels of the compositions of the invention are administered so as to provide therapeutic benefits against the secondary harmful inflammatory effects of inflammation. By an "efficacious level" of a composition of the invention is meant a level at which some relief is afforded to the patient who is the recipient of the treatment. By an "abnormal" host inflammatory condition is meant a level of inflammation in the subject at a site which exceeds the norm for the healthy medical state of the subject, or exceeds a desired level. By "secondary" tissue damage or toxic effects is meant the tissue damage or toxic effects which occurs to otherwise healthy tissues, organs, and the cells therein, due to the presence of excessive selectin, and especially L-selectin, adhesion events, including as a result of a "primary" stimulus elsewhere in the body.

In the methods of the invention, infusion of the compositions of the invention into a patient results in a lessening of the ability of selectin-expressing leukocytes to "roll" and thus attach to the endothelium, thus preventing or inhibiting adherence of such cells to the site of the inflammation and the localized damage to the endothelium, and thus preventing undesired lymphocyte trafficking or influx into the affected tissues or cells.

Accordingly, the pharmaceutical compositions of the invention provide for compositions containing the synthetic carbohydrates of the invention, in amounts sufficient to antagonize (fully or partially) the patient's native selectin, and especially L-selectin, binding to biological targets of such selectin in such patient, and specifically to endothelial cells.

The oligosaccharides of the invention may be conjugated, either chemically or by genetic engineering, to fragments of other agents which provide a targeting of such selectin-binding compounds to a desired site of action. Alternatively, other compounds may be conjugated, either chemically or by genetic engineering, to the oligosaccharides of the invention so as to enhance or provide additional properties to such oligosaccharides or compositions containing the same, especially properties which enhance the compound's ability to promote relief of adhesion-mediated toxic effects, or promote clearance of the compound from the bloodstream, or other advantageous properties.

Amounts and regimens for the administration of selectin-binding oligosaccharides and compositions comprising the oligosaccharides of the invention can be determined readily by those with ordinary skill in the clinical art of treating inflammation-related disorders such as arthritis, tissue injury and tissue rejection. Generally, the dosage of the composition of the invention will vary depending upon considerations such as: type of synthetic carbohydrate employed; age; health; medical conditions being treated; kind of concurrent treatment, if any, frequency of treatment and the nature of the effect desired; extent of tissue damage; gender;

duration of the symptoms; and, counter indications, if any, and other variables to be adjusted by the individual physician. A desired dosage can be administered in one or more applications to obtain the desired results. Pharmaceutical compositions containing the oligosaccharides of the invention, such as the divalent sLexLex- and sLexLexLex-saccharides, may be provided in unit dosage forms.

Preferably, the divalent glycans of the present invention, e.g., the sLexLex and sLexLexLex oligosaccharides are administered to a patient in a dosage sufficient to achieve a 0.1 nM to 10,000 nM serum concentration, or higher if desired, in said patient. More preferably, the synthetic divalent sLex-containing polylactosamines of the present invention are administered to a patient in a dosage sufficient to achieve a 0.1 nM to 500 nM serum concentration in said patient.

The pharmaceutical compositions containing the synthetic oligosaccharides of the invention can be administered in any appropriate pharmacological carrier for administration. They can be administered in any form that effects prophylactic, palliative, preventative or curing conditions of selectin, and especially L-selectin, mediated events in humans and animals. For the purpose of definition, it is intended that the expression "a method of treatment" of a disease, and like expressions, throughout the specification and claims, be taken to include a method for the prevention of such disease.

The method of the invention is useful for the prevention of rejection or inflammation of transplanted tissue or organs of any type, for example, heart, lung, kidney, liver, skin grafts, tissue grafts, etc.

The compositions of the invention, may include sterile aqueous or non-aqueous solvents, suspensions and emulsions, especially when intended for parenteral administration. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The compositions of the invention may also be administered by means of pumps, or in sustained-release form, especially, when the primary injury is prolonged or delayed rather than acute. An example in which the primary injury is often prolonged or delayed rather than acute is an infection or sprain wherein the damage to the tissue or muscle is not revealed (or persists) until days after the primary infection or damage. The selectin-binding molecules of the invention may also be delivered to specific organs in high concentration by means of suitably inserted catheters, or by providing such molecules as a part of a chimeric molecule (or complex) which is designed to target specific organs.

Administration in a sustained-release form is more convenient for the patient when repeated injections for prolonged periods of time are indicated. For example, it is desirable to administer the compositions of the invention in a sustained-release form when the methods of the invention are being used to treat a genetic or chronic inflammatory disease that is based upon a selectin-mediated disorder, so as to maximize the comfort of the patient.

The compositions of the invention can be employed in dosage forms such as tablets, capsules, powder packets, or liquid solutions for oral administration if the biological activity of the active multimeric carbohydrate is not destroyed by the digestive process and if the characteristics of the compound allow it to be absorbed across the intestinal tissue.

The pharmaceutical compositions of the present invention are manufactured in a manner which is in itself known, for example, by means of conventional mixing, granulating, dragee-making, dissolving, lyophilizing or similar processes. The compositions of the present invention, in and of themselves, find utility in the control of inflammation-mediated physiological damage, be it chronic or acute. The compositions of the invention obviate the body's own mechanisms for recognizing selectin-mediated adhesion to its maximum potential.

In intravenous dosage form, the compositions of the present invention have a sufficiently rapid onset of action to be useful in the acute management of potential tissue damage.

Additionally, a low potency version is useful in the management of mild or chronic selectin-mediated inflammatory disorders.

The affinities of the glycans of the invention towards rat lymphocyte L-selectin were analyzed with the in vitro Stamper-Woodruff binding assay. The divalent glycans sLexLN and sLexLex significantly reduce lymphocyte binding, the latter revealing $IC_{50}$ of 50 nM. The important control saccharides, carrying at the distal termini the fucose-free sLN-residues instead of the sLex-epitopes are consistently without any inhibitory effect. The present invention emphasizes the crucial role of the terminal sLex-epitopes in the recognition of L-selectin, and show that the additional, inner Lex residue enhances the affinity of the ligands.

The following examples represent the enzymatic synthesis of complex oligosaccharides in sufficiently large amounts (as described in the examples) such that one can routinely conduct the types of experiments described in this application. The present invention overcomes previous difficulties in this regard.

The following examples are merely intended to illustrate the present invention and not in any way to limit its scope.

EXAMPLES

Example 1

Materials and Methods

Acceptor Saccharides

The synthesis of glycans 1–4 (bolded numbering corresponds to glycan structures in FIG. 1) was previously described in co-pending U.S. application Ser. No. 08/722,573, the entire contents of which is hereby incorporated by reference. The decasaccharide LNβ1,3'LNβ1,3'(LNβ1,3'LNβ1,6')LN was synthesized essentially as described (Niemela, R. et al., *FEBS Lett.* 367:67–72 (1995)).

Enzymatic Reactions

Enzymatic reactions of the glycans were carried out according to published methods; β(1,4) galactosylation as described (Brew, *Proc. NatL. Acad. Sci.* 59:491–497 (1968)), α(2,3) sialylation as described (Maaheimo, H. et al., *Eur. J. Biochem.* 234.616–625 (1995)), β1,6-N-acetylglucosaminylation (Leppanen, A. et al., *Biochemistry* 36.7026–7036) and α(1,3)fucosylation as described (Natunen, J. et al., *Glycobiol* 4:577–583 (1994)).

Chromatographic Methods

Gel filtration in a column of Superdex 75HR75 10/70 column (Pharmacia, Sweden) was performed in 50 mM NH$_4$HCO$_3$ as described previously (Niemela, R. et al., *FEBS Lett.* 367:67–72 (1995)). Anion exchange chromatography on a MonoQ (5/5) column (Phartnacia) was performed as described (Maaheimo, H. et al., *Eur. J. Biochem.* 234:616–625 (1995)). The amount of oligosaccharides was estimated by UV-monitoring of Superdex chromatograms; the appropriate peak areas were related to data obtained with GlcNAc and NeuNAc standards.

NMR Spectroscopy

Prior to NMR experiments the saccharides were twice lyophilized from D$_2$O and then dissolved in 600 μl 99.96% D$_2$O (C.I.L., MA, USA). The experiments were performed on a Varian Unity-500 spectrometer at 23° C. In recording the proton spectra, a modification of the WEFT sequence was used. The $^1$H chemical shifts were referenced to internal acetone signal set to 2.225 ppm.

Mass Spectroscopy

Matrix assisted laser desorption/ionisation time-of-flight mass spectroscopy (MALDI-TOF MS) was performed with a BIFLEX™ mass spectrometry (Bruker-Franzen Analytik, Bremen, Germany) using a 337 nm nitrogen laser. The sialylated oligosaccharides were measured in the linear negative ion mode with delayed extraction using 2,4,6-trihydroxyacetophenone (THAP) matrix. Samples were prepared by mixing 0.5 μl of saccharide solution (5–10 pmol oligosaccharide in water) and 0.5 μl of THAP matrix (3 mg/ml in acetonitrile/20 mM aqueous ammonium citrate, 1:1 v/v) on the target plate, and the droplets were immediately dried under vacuum to produce a homogenous thin matrix preparation (Papac, D. I. et al., *Analytical Chemistry* 68:3215–23 (1996)). External calibration was performed with angiotensin 2 and ACTH clip peptide (Sigma).

Lymphocyte Binding to High Endothelial Venules (HEVS)

Lymphocytes were isolated from mesenterical lymph nodes of WF or DA rats and used immediately in the assay after isolation and pretreatment. Single cell suspensions were made by mechanical disaggregation in RPMI 1640 medium (Gibco) supplemented with Hepes (25 mM) and 0.5% fetal calf serum (FCS), and the cells were passed through a 50 μm pore size mesh (Turunen, J. P. et al., *J. Exp. Med.*, 182:1133–1142 (1995)). Lymphocytes were over 99% of purity as quantitated by cytocentrifuge preparations.

8 pm thick frozen sections from lymph nodes of DA- and WF-rats were cut and either used within one hour for the binding assay or stored at -70° C. The stored slides were fixed for 20 minutes in 1% paraformaldehyde in 0.1 M sodium cacodylate, pH 7.3 and washed in phosphate buffered saline immediately when they were removed from the freezer.

In the Stamper-Woodruff assay 3×10$^6$ lymphocytes in 100 μl of RPMI containing 0.5% FCS were put on a frozen section inside a 23 mm wax circle, and rotated for 30 min at +4° C. After the assay, the non-adherent lymphocytes were gently removed from the slide with an absorbent paper, the slides were fixed in 1.5% glutaraldehyde at +4° C. overnight, and stained for 40 min with thionine. The excess thionine was gently washed away using PBS, and the slides were mounted with Aquamount Mountant, (BHD Limited, Poole, England). The number of bound lymphocytes was calculated per high endothelial venules and 50 to 100 vessels were identified from each sample. It has previously been shown that this assay measures primarily L-selectin dependent events as the lymphocyte adhesion could be inhibited by anti- L-selectin antibodies, L-selectin-IgG fusion protein, and Ca$^{2+}$-depletion (Toppila, S. et al., *Eur. J. Immunol.* 27.1360–1365 (1997); Turunen, J. P. et al., *J. Exp. Med* 182(4):1133–1141 (1995)).

Example 2

Synthesis and Characterization of Divalent Sialoglycans (Bolded Numbering Corresponds to Glycan Structures in FIG. 1)

Oligosaccharides representing a family of divalent sialyl LN- (sLN) and sialyl Lewis x- (sLex) containing glycans as well as divalent sLNLN-, sLexLN-, sLNLex- and sLexLex-containing glycans were enzymatically synthesized. The synthesis of glycans 1–4 (bolded numbering corresponds to glycan structures in FIG. 1) was previously described in co-pending U.S. application Ser. No.08/722,573, the entire contents of which is hereby incorporated by reference. In the following examples, Neu-Nac: sialic acid; Gal: galactose; Fuc: fucose; GlcNac: N-acetylglucosamine.

Synthesis of Glycan 5

Glycan 5 was constructed by enzymatic α2,3-sialylation of the decasaccharide LNβ1,3'LNβ1,3'(LNβ1,3'LNβ1,6')LN by treatment with CMP-NeuNAc and human placental microsomes which contain α2,3-sialyltransferase activity (Seppo, A. et al., *Glycobiology* 6:65–71 (1996)). The purified reaction product chromatographed in anion exchange chromatography on a monoQ (5/5) column like the disialylated glycan 1. It gave a proton NMR-spectrum (FIG. 2, see Table 1) that established its structure as SAα2,3'LNβ1, 3'LNβ1,3' (SAα2,3'LNβ1,3'LNβ1,6')LN. The H1 and H-3 resonances of galactose residues 9 and 10 of glycan 5 at 4.557 ppm and 4.116 ppm, respectively, are highly characteristic to NeuNAcα2,3Gal units in primary polylactosamine chains (Kamerling & Vliegenthart, *Biological Magnetic Resonance*, Berliner & Reuben, editors, vol. 10, Plenum Press, New York & London (1992), pp. 1–287); Maaheimo, H. et al., *Eur. J. Biochem.* 234:616–625 (1995)). The chemical shifts of the signals for H3 ax- and H3 eq-protons, at 1.799 and 2758 ppm, respectively, were also characteristic to α2,3-linked NeuNAc (Kamerling & Vliegenthart, *Biological Magnetic Resonance*, Berliner & Reuben, editors, vol. 10, Plenum Press, New York & London (1992), pp. 1–287). The integrals of both these signals corresponded to two proton equivalents, compared to one proton H-1 resonance of β1,6-linked GlcNAc (4) (see Table 1 for the numbering of the monosaccharide residues). The presence of two sialic acid residues was confirmed also by the absence of a signal around 4.479 ppm, a characteristic chemical shift for H1 of terminal galactoses, indicating that both branches were sialylated.

Figure 3:
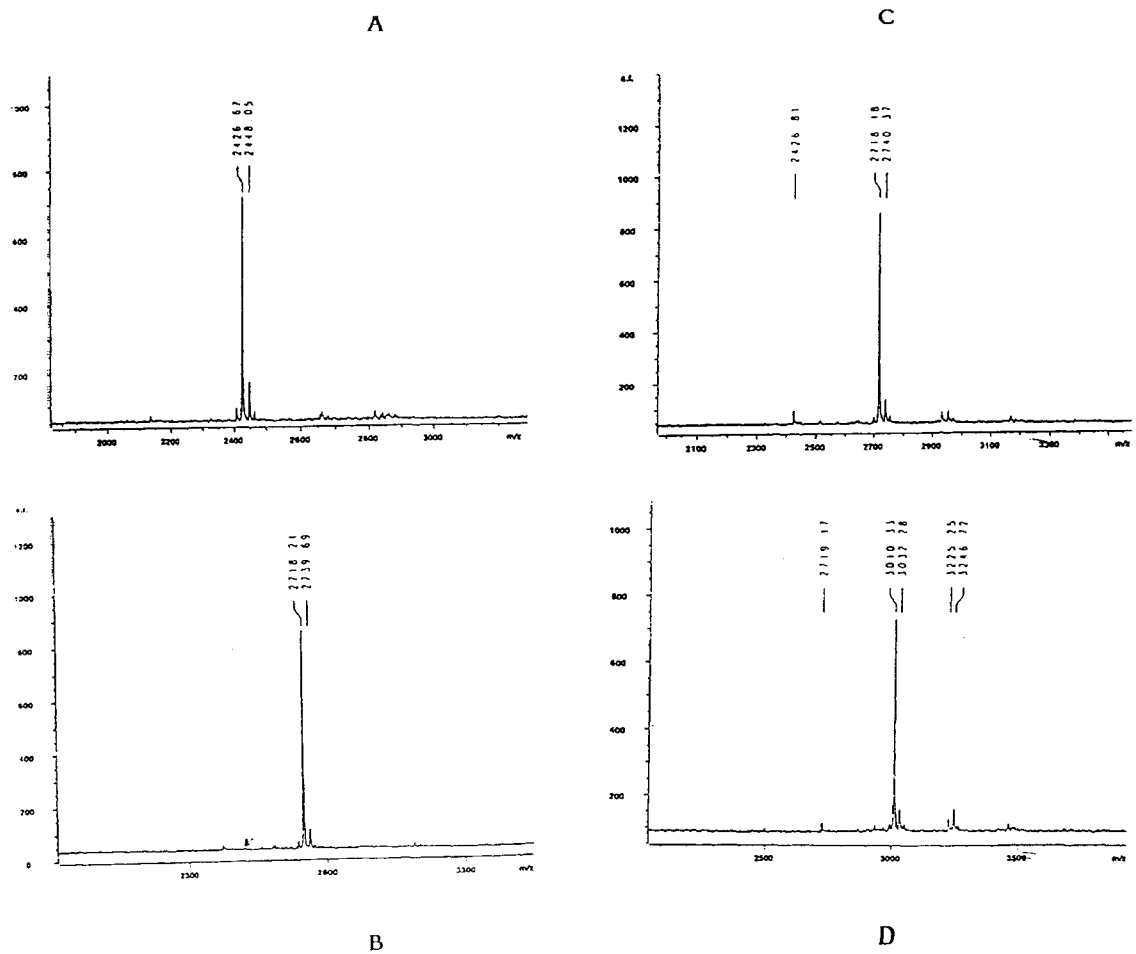
FIG. 3 (panels a–d). MALDI-TOF mass spectra of sialoglycans. a) spectrum of glycan 5, b) spectrum of glycan 6, c) spectrum of glycan 7, d) spectrum of glycan 8.

In MALDI-TOF mass spectrometry glycan 5 revealed a major signal at m/z 2426.7 that was assigned to [M-H]$^-$ (calc. average m/z 2426.2). A minor peak at m/z 2448.0 was signed to [M-2H+Na]$^-$ (calc. average m/z 2448.2) (FIG. 3a).

Synthesis of Glycan 6

Figure 2:
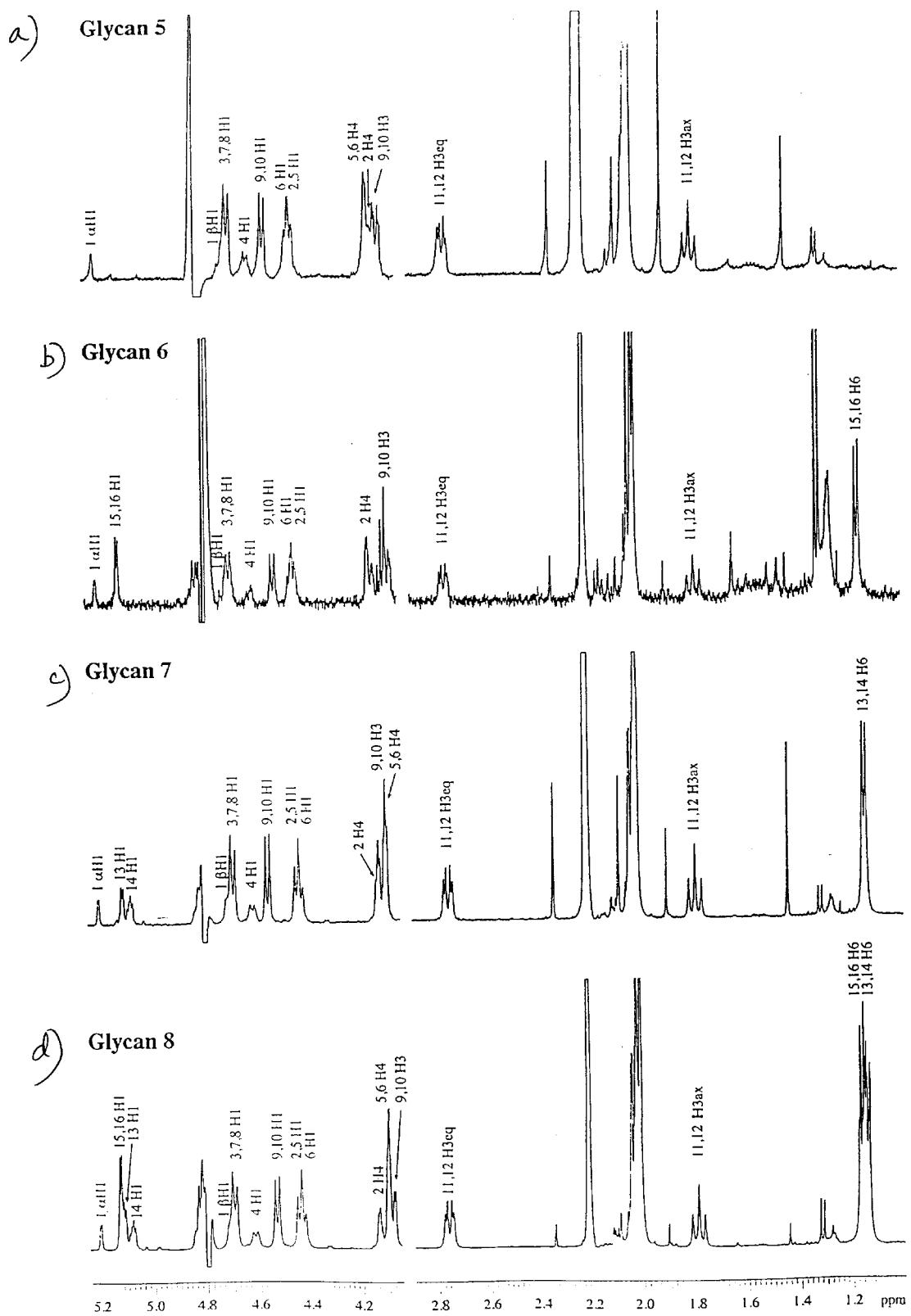
FIG. 2 (panels a–d). Expansions of 500 MHZ $^1$H-NMR spectra of glycans. a) spectrum of glycan 5, b) spectrum of glycan 6, c) spectrum of glycan 7, d) spectrum of glycan 8.

Glycan 6 was synthesized from the decasaccharide LNβ1, 3'LNβ1,3'(LNβ1,3'LNβ1,6')LN by introducing "protective" β1,6-bonded branch to the inner galactose of both the 3- and 6-bonded branches (Niemela, R et al., *Glycoconjugate J.* 12:36–44 (1995) by using the mid-chain β1,6-acetylglucosyltransferase activity present in rat serum. The resulting dodecasaccharide was purified, enzymatically α2,3-sialylated as above, and α1,3 fucosylated with GDP-fucose and partially purified α1,3/4 fucosyltransferase from human milk. This treatment transfers fucosyl units only to the distal, sialylated units. The product was then treated with α-N-acetylhexosaminidase to remove the "protective" GlcNac-residues. Proton NMR-spectroscopy confirmed that the final product had the structure of glycan 6 (FIG. 2, see Table I). In particular, the resonances characteristic to the fucose and sialic acid residues of sLex-determinants were observed. These include the H-1 and H-6 resonances of the fucose residues 15 and 16 at 5.121 ppm and 1.168 ppm, respectively, as well as the H-3 eq and H-3 ax resonances of the sialic acid. The latter resonances originating from sLex-determinants are distinct from those originating from sLN-epitopes. Even the H-3 signals of the galactose residues 9 and 10 in glycan 6 were distinct from those of glycan 5, and were detected at 4.086 ppm which is characteristic to sLex (Maaheimo, H. et al., *Eur. J. Biochem.* 234:616–625 (1995); Seppo, A. et al., *Glycobiology* 6:65–71 (1996)). By contrast, features typical to the VIM-2 sequences sLNLex were not observed.

In MALDI-TOF mass spectrometry, glycan 6 revealed a major signal at m/z 2718.2 that was assigned to [M-H]$^-$ [calc. average m/z 2718.5). A minor peak at m/z 2739.7 was assigned to [M-2H+Na]$^-$ (calc. average m/z 2740.5) (FIG. 3*b*).

Synthesis of Glycan 7

Glycan 7 was synthesized from the octasaccharide GNβ1,3'LNβ1,3'(LNβ1,3'LNβ1,6')LN (Wilkman, A. et al., *Carbohydrate Res.* 226:155–174 (1992)) by α1,3 fucosylation at the inner GlcNAc residues of both brances as above. The resulting decasaccharide was then purified and β1,4-galactosylated with bovine milk β1,4-galactosyltransferase. The purified product was finally α2,3 sialylated as above. The NMR-spectrum (FIG. 2, Table I) established the structure of the sialylated product as glycan 7. The spectrum reveals H-1 resonances originating from the ten monosaccharides of the polylactosamine backbone together with "reporter group" signals of two α1,3-bonded fucose residues and two α2,3-bonded sialic acid units. These aspects of the spectrum resemble closely that of the simple VIM-2 hexasaccharide NeuNAcα2,3Gal 1-4GlcNAcβ1-3Galβ1-4(Fucα1-3)GlcNAc (Kashem, M. A. et al., *Carbohydrate Research* 250:129–44 (1993)). In addition, there are resonances of (i) one H-4 proton that belongs to the 3,6-bisubstituted galactose in the Lexβ1-3'Lexβ1-6'LN unit, and (ii) two H-4 protons of 3-substituted Lex-galactose, and (iii) two H-3 protons of α2,3-sialylated galactose residues. The H-3ax and H-3eq signals of the sialic acid and H-1 and H-3 signals of galactoses 9 and 10 in glycan 7 resemble those of glycan 5, confirming that the sialylated N-acetyl lactosamine units in glycan 7 are not fucosylated.

In MALDI-TOF mass spectrometry glycan 7 revealed a major signal at m/z 2718.2 that was assigned to [M-H]$^-$ [calc. average m/z 2718.5). A minor peak at m/z 2740.4 was assigned to [M-2H+Na]$^-$ (calc. average m/z 2740.5) (FIG. 3*c*).

Synthesis of Glycan 8

Glycan 8 was synthesized from glycan 5 by exhaustive α1,3 fucosylation as above. The branch-bearing LN-unit does not accept fucosyl units under these conditions (Niemela, R. et al., *FEBS Lett.* 367:67–72 (1995)). The NMR-spectrum confirmed that a tetrafucosyl glycan was formed (FIG. 2 and Table I). The integrals of H1 and H-6 resonances of glycan 8 compared that of the H-1 signal of GlcNAc(4) showed that four fucose residues were present. The H-3ax and H-3eq signals of the sialic acid residues were typical sLex signals and the H-4 signals of galactose(5) and galactose(6) were typical to mid chain sLex units.

In MALDI-TOF mass spectrometry, glycan 8 revealed a major signal at m/z 3010.3 that was assigned to [M-H]$^-$ [calc. average m/z 3010.8). A minor peak at m/z 3032.3 was assigned to [M-2H+Na]$^-$ (calc. average m/z 3032.8) (FIG. 3*d*).

TABLE 1

$^1$H-NMR Chemical shifts (ppm) of structural reporter groups of asialo-5[b)] and glycans 5–8.

| Reporter group | residue[a)] | asialo-5[b)] | 5 | 6 | 7 | 8 |
|---|---|---|---|---|---|---|
| H-1 | 1α | 5.207 | 5.208 | 4.208 | 5.206 | 4.208 |
|  | 1β | 4.724 | 4.724 | 4.723 | 4.712 | 4.713 |
|  | 2 | 4.455 | 4.453[d)] | 4.454[c)] | 4.449 | 4.448 |
|  | 3[c)] | 4.698/4.693 | 4.693 | 4.691 | 4.693 | 4.69 |
|  | 4[c)] | 4.622/4.614 | 4.623/4.613 | 4.620 | 4.619/4.612 | 4.618/4.613 |
|  | 5 | 4.467 | 4.445[d)] | 4.448[c)] | 4.449 | 4.448 |
|  | 6 | 4.451 | 4.465 | 4.465 | 4.434 | 4.433 |
|  | 7, 8 | 4.702 | 4.693 | 4.698 | 4.693 | 4.696 |
|  | 9, 10 | 4.479 | 4.557 | 4.531 | 4.559 | 4.534 |
|  | 13 | — | — | — | 5.112 | 5.112 |
|  | 14[c)] | — | — | — | 5.089/5.076 | 5.089/5.76 |
|  | 15, 16 | — | — | 5.121 | — | 5.128 |
| H-3 | 9, 10 | N.D. | 4.116 | 4.086 | 4.117 | 4.086 |
| H-3ax | 11, 12 | — | 1.799 | 1.795 | 1.799 | 1.795 |
| H-3eq | 11, 12 | — | 2.758 | 2.764 | 2.758 | 2.764 |
| H-4 | 2 | 4.146 | 4.146 | 4.144 | 4.135 | 4.136 |
|  | 5 | 4.156 | 4.159 | N.D. | 4.100 | 4.102 |
|  | 6 | 4.156 | 4.159 | N.D. | 4.100 | 4.102 |
| H-6 | 13, 14 | — | — | — | 1.150 | 1.147 |
|  | 15, 16 | — | — | 1.168 | — | 1.168 | a) Numbering of the residues is as follows

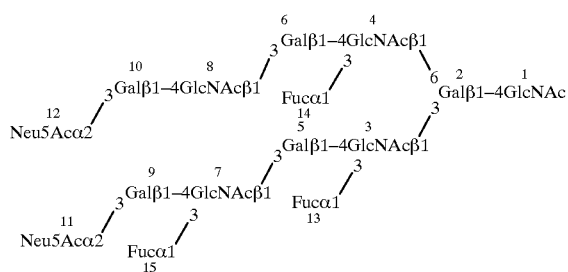

b) Data from Niemela, R. et al., *FEBS Lett.* 367:67–72 (1995)
c) The two values correspond to the two anomeric forms of residue 1
d, e) Assignments may have to be exchanged
N.D. Not determined.

Example 3

Figure 4:
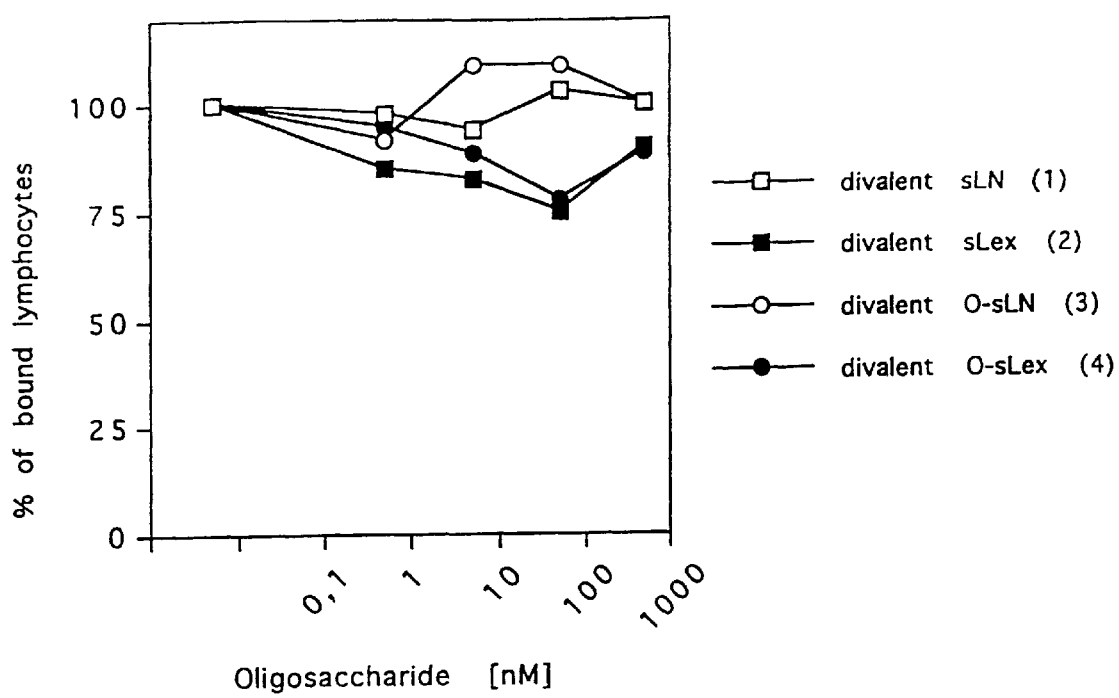
FIG. 4. Effect of divalent short-branched glycans 1–4 on in vitro lymphocyte adhesion to high endothelial venules of peripheral rat lymph nodes. In the assay the divalent sLex-glycan 2 and O-linked, divalent sLex-glycan 4 inhibited lymphocyte adhesion to 75% of the background value. The corresponding non-fucosylated polylactosamines (glycans 1 and 3, respectively) did not inhibit adhesion. The mean of three independent experiments are shown. The SEM values never exceeded 15% (not marked for clarity).
Figure 5:
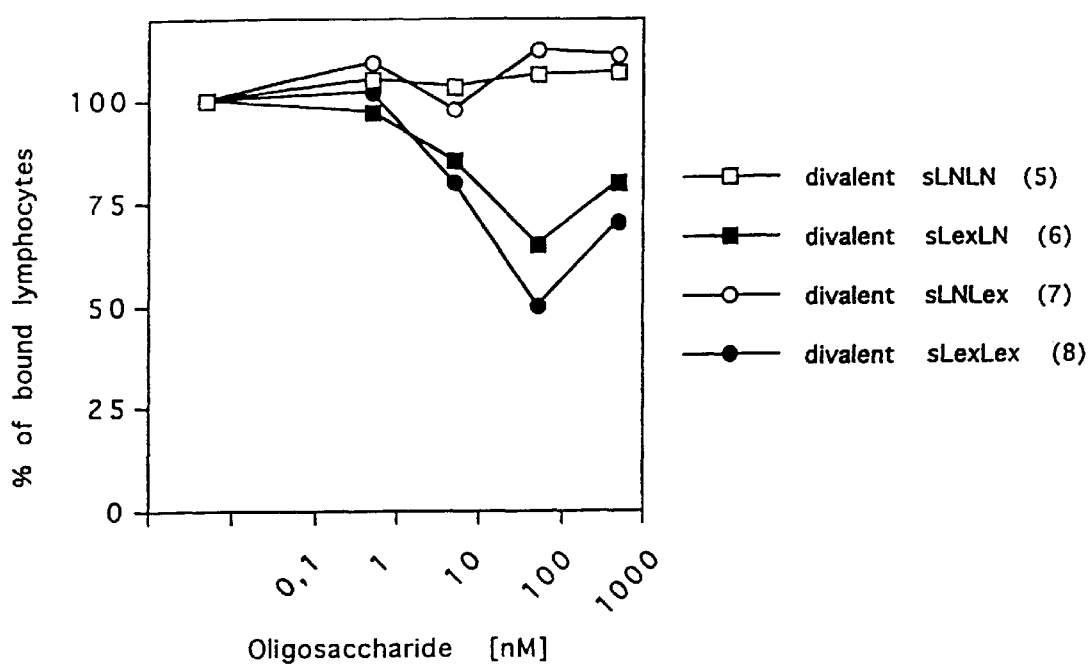
FIG. 5. Effect of long-branched glycans 5–8 on in vitro lymphocyte adhesion to high endothelial venules of peripheral rat lymph nodes. In the assay the divalent sLexLN (glycan 6) and the divalent sLexLex (glycan 8) glycans inhibited lymphocyte adhesion to 65% and 50% of the background value, respectively. The non-fucosylated polylactosamines (glycans 5 and 7) did not show inhibitory effects. The mean of three independent experiments are shown. The SEM values never exceeded 15% (not marked for clarity).
Figure 6:
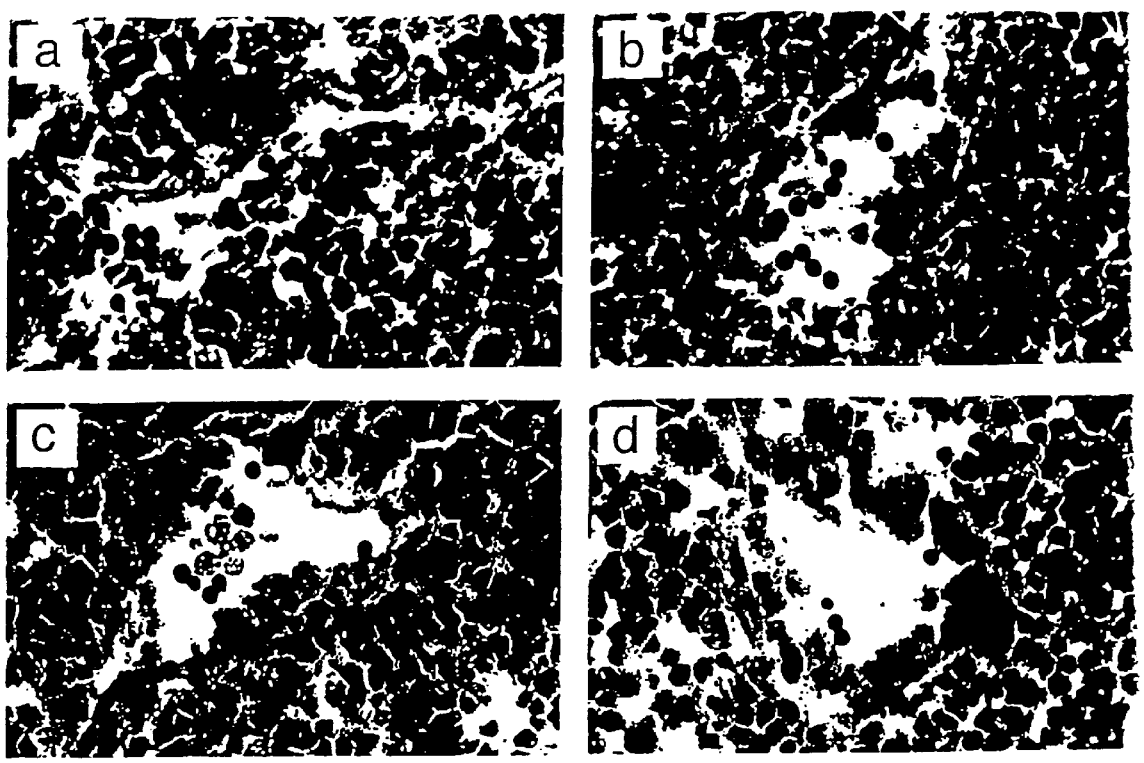
FIG. 6 (panels a–d). Binding of lymphocytes to high endothelial venules (HEV) of peripheral rat lymph nodes. Panel (a) shows the binding of non-treated lymphocytes to HEV. Panel (b) shows that there was no effect of the divalent non-fucosylated sLN (glycan 1) on the lymphocyte binding. Panel (c) shows the marginal effect of divalent sLex (glycan 2) on the number of bound lymphocytes on lymph node HEV. Panel (d) shows that the best inhibitor was the divalent sLexLex (glycan 8) which inhibited 50% of the adhesion at 0.1 mM concentration.

Inhibition of Lymphocyte Binding by Divalent Glycans Containing sLN-, sLex-, sLNLN-, sLNLex- and sLexLex-epitopes Lymphocyte adhesion was studied in a well documented L-selectin-dependent Stamper-Woodruff assay where frozen sections of lymph nodes were prepared, lymphocytes were placed on top of them, adhesion was permitted on a rotator and the number of adherent cells were quantitated visually. The panel of glycans studied is shown in FIG. 1. The inventors found that glycans 2 and 4 at 50 nM reduced L-selectin-dependent lymphocyte adhesion to HEVs down 75% of the control value (FIG. 4). At the same time glycans 1 and 3 representing corresponding fucose-free sialylated N-acetyllactosamines were without any effect. Glycan 6 with sLex units at the end of both extended arms (sLexLN) reduced lymphocyte adhesion down to 70% of normal values at 50 nM (FIG. 5). The most potent inhibitory oligosaccharide was the divalent sLexLex (glycan 8). It reduced lymphocyte adhesion down to 50% of normal values at 50 nM (FIG. 5). Concomitantly, the fucose-free divalent sLNLN (glycan 5) and the divalent sLNLex (glycan 7) had no effect in lymphocyte binding to HEV. Taken together these data provide evidence that the divalent sLex-Lex glycan 8 posessed outstanding inhibitory activity in the L-selectin-dependent cell adhesion assay.

Among the glycans, the divalent sLexLex glycan 8 was the most potent inhibitor of lymphocyte adhesion, suggesting that it might bind to several L-selectin molecules on the lymphocyte surface.

Example 4

Tissue-Specific Inhibition of Lymphocyte Binding to Endothelium

Figure 7:
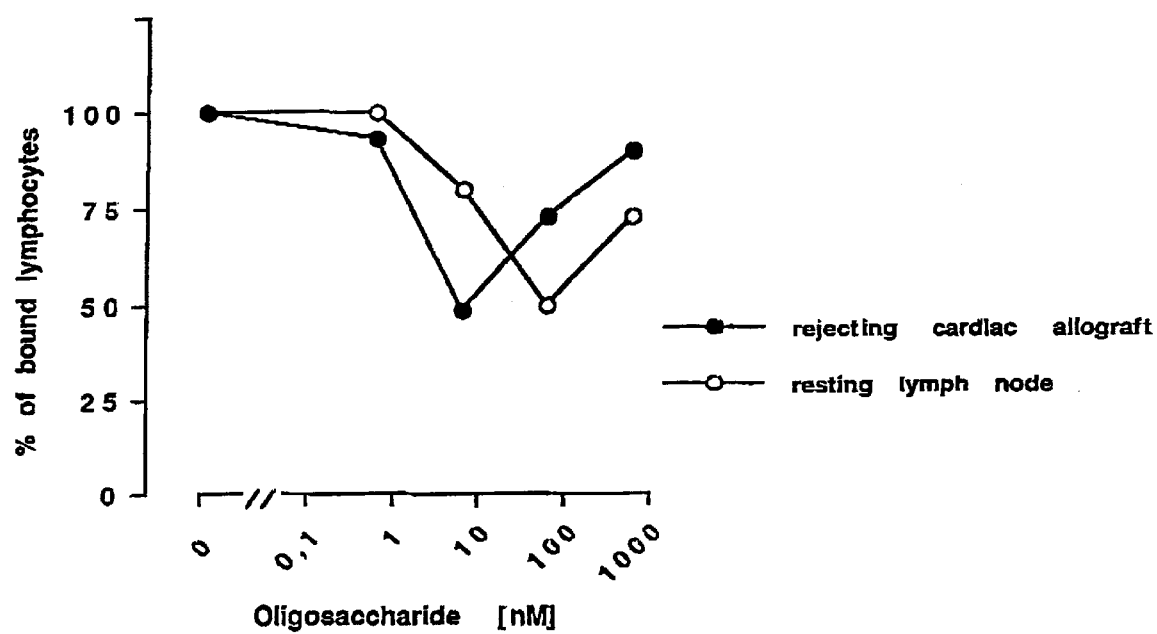
FIG. 7. Effect of the divalent sLexLex (glycan 8) on ex vivo lymphocyte adhesion to endothelium of a rejecting transplant and lymph node HEV. The mean of three independent experiments is shown. The SEM values never exceeded 15% (not marked for clarity).

The putative role of the glycan 8 as an anti-inflammatory agent during acute inflammations was studied by performing heart transplantations between MHC-incompatible inbred rat strains DA and WF. As previously shown the drug-unmodified grafts undergo severe acute rejection manifested by a heavy lymphocyte infiltrate starting within a few days after transplantation (Turunen, J., et al., *J. Exp. Med.* 182:1133–1142 (1995), Renkonen, R., et al., *Cell. Immunol.* 77:188–195 (1983)). The hearts were removed at day 3, and the lymphocyte binding assay was performed in the presence of different concentrations of the divalent sialylLexLex-glycan (glycan 8). The presence of this saccharide reduced the number of endothelium-bound lymphocytes to half of the control value already at 5 nM, a concentration ten times lower than the $IC_{50}$-value at the lymph node HEV (see FIG. 7). This data suggests that a therapeutic concentration window of the divalent sialylLexLex-glycan (glycan 8) exists, where the lymphocyte traffic is inhibited at sites of inflammation, while the normal lymphocyte recirculation via lymph nodes will not be altered.

Glycan 8 inhibited lymphocyte adhesion to endothelium of a rejecting heart transplant at lower concentrations than the adhesion to peripheral lymph node HEV. Accordingly, by applying low concentrations of glycan 8 in vivo it is possible to inhibit lymphocyte recruitment into rejecting cardiac allografts without severely altering the normal lymphocyte homing into peripheral lymph nodes. The site-specific action of glycan 8 as an inhibitor of extravasation of lymphocytes is one of the very first examples of reported organ-selective immunosuppression.

Example 5

Treatment of a Patient with sLex

A patient diagnosed with an inflammatory condition is treated with a composition comprising a divalent sLex, e.g. the divalent sdiLex or striLex saccharide. The composition is in a pharmaceutically acceptable excipient at a sufficient dose to block lymphocyte binding to the correspondent oligosaccharides on the endothelial cell surface. The composition is given in a regime such that a serum concentration is achieved in about the nanomolar to micromolar range until the condition is sufficiently ameliorated.

When administered to the patient, the composition is formulated in any manner which makes it suitable for oral, parenteral, nasal, enteric or rectal administration with a pharmaceutically acceptable excipient or vehicles, e.g., isotonic saline, in accordance with conventional pharmaceutical practice. The dosage level of the reagent will be sufficient to provide an anti-inflammatory effect by the blocking of selectin, and especially L-selectin-mediated adhesion events in the patient.

The composition and method of the invention are suitable for treating any condition involving a selectin, and especially an L-selectin-mediated adhesion increased inflammatory reaction. Thus, the reagent is useful for treating such conditions as tissue rejection, arthritis, an infection, especially local infections, dermatoses, inflammatory bowel diseases, autoimmune diseases, etc.

By an "efficacious level" of a composition of the invention is meant a level at which some relief is afforded to the patient who is the recipient of the treatment. By an "abnormal" host inflammatory condition is meant a level of inflammation in the subject at a site which exceeds the norm for the healthy medical state of the subject, or exceeds a desired level. By "secondary" tissue damage or toxic effects is meant the tissue damage or toxic effects which occurs to otherwise healthy tissues, organs, and the cells therein, due to the presence of excessive selectin, and especially L-selectin, adhesion events, including as a result of a "primary" stimulus elsewhere in the body.

Infusion of the compositions of the invention into a patient is thought to result in a lessening of the ability of selectin-expressing leukocytes to "roll" and thus attach to the endothelium, thus preventing or inhibiting adherence of such cells to the site of the inflammation and the localized damage to the endothelium, and thus preventing undesired lymphocyte trafficking or influx into the affected tissues or cells.

Accordingly, the pharmaceutical compositions of the invention are administered in amounts sufficient to antagonize (fully or partially) the patient's native selectin, and especially L-selectin, binding to biological targets of such selectin in such patient, and specifically to endothelial cells.

Amounts and regimens for the administration of selectin-binding carbohydrates and compositions of the invention can be determined readily by those with ordinary skill in the clinical art of treating inflammation-related disorders such as arthritis, tissue injury and tissue rejection. Generally, the dosage of the composition of the invention will vary depending upon considerations such as: type of synthetic carbohydrate employed; age; health; medical conditions being treated; kind of concurrent treatment, if any, frequency of treatment and the nature of the effect desired; extent of tissue damage; gender; duration of the symptoms; and, counterindications, if any, and other variables to be adjusted by the individual physician. A desired dosage can be administered in one or more applications to obtain the desired results.

Example 6

Treatment of a sLex Positive TRumor Metastasis with sLEX

Carbohydrate-containing molecules have been implicated in many disease states, including auto-immune diseases, inflammatory conditions, peptic ulcers, infectious diseases and cancer. Indeed, changes in the surface carbohydrate molecules on human tumor cells has made it possible to identify human glycoprotein "cancer antigens" for many tumor types, including melanomas, gliomas, neuroblastomas and breast, pancreatic, lung, prostate and kidney cancers. One member of the lectin family of carbohydrate binding proteins has been strongly associated with both metastasis and shortened survival in breast cancer patients. The terminal sugar of the carbohydrate molecule to which the lectin binds has been identified as N-acetyl galactosamine. Moreover, the same N-acetyl galactosamine sugar has been found on several other tumor types, including prostate, stomach, and colorectal cancer cells, and has been associated with increased metastasis or reduced survival in each case (Hughes, S., *Scrip*, April 1994, pp 28–31). Other studies have shown that colon-carcinoma cell lines adhere to certain selectins via sialyl Lewis x and sialyl Lewis a oligosaccharides (Majuri, M.-L., et al., *Int. J. Cancer* 63:551–559 (1995); Majuri, M.-L., et al., *Biochem. Biophys. Res. Comm.* 182(3):1376–1382 (1992)).

Accordingly, the synthetic divalent sLex containing polylactosamines of the present invention can be used to inhibit the metastasis of sLex positive tumor cells. Briefly, a patient diagnosed with such a tumor is treated with a composition comprising a divalent sLex e.g., the sLexLex- or sLexLexLex-saccharide. The composition is in a pharmaceutically acceptable excipient at a sufficient dose to inhibit the metastasis of the sLex positive tumor cells by blocking the binding of the tumor cells to natural sLex. An efficacious level of the composition is given in a regime such that a serum concentration is achieved in about the nanomolar to micromolar range until the condition is sufficiently ameliorated.

When administered to the patient, the composition is formulated in any manner which makes it suitable for oral, parenteral, nasal, enteric or rectal administration with a pharmaceutically acceptable excipient or vehicles, e.g., isotonic saline, in accordance with conventional pharmaceutical practice. The dosage level of the reagent will be sufficient to provide an anti-metastasis effect by the blocking of selectin, and especially L-selectin-mediated adhesion of the tumor cells in the patient.

By an "efficacious level" of a composition of the invention is meant a level at which some relief is afforded to the patient who is the recipient of the treatment.

The pharmaceutical compositions of the invention are administered in amounts sufficient to antagonize (fully or partially) the patient's native selectin, and especially L-selectin, binding to biological targets of such selectin in such patient, and specifically to sLex positive tumor cells.

Amounts and regimens for the adminstration of selectin-binding carbohydrates and compositions of the invention can be determined readily by those with ordinary skill in the clinical art of treating cancer-related disorders. Generally, the dosage of the composition of the invention will vary depending upon considerations such as: type of synthetic carbohydrate employed; age; health; medical conditions being treated; kind of concurrent treatment, if any, frequency of treatment and the nature of the effect desired; extent of tissue damage; gender; duration of the symptoms; and, counterindications, if any, and other variables to be adjusted by the individual physician. A desired dosage can be administered in one or more applications to obtain the desired results.

Example 7

Treatment of an Infection with sLex

The use of sLex as an anti-infective is based on the observation that oligosaccharides are present on the surface of all mammalian cells, and are used by bacteria, viruses, and other infectious micro-organisms to enter those cells (Hughes, S., *Scrip*, April 1994, pp28–32). For example, human sialyl Lewis x antigen is highly expressed on the cell surface of Streptococcus gallolyticus, which is a cause of infective endocarditis in humans (Hirota, K., et al., *Lancet* 347:760 (1996); Hirota, K., et al., *FEMS Immunol. & Med. Microbiol.* 12:159–164 (1995). Thus, flooding the body with one particular type of oligosaccharide is one possible therapeutic approach to particular infectious diseases (Hughes, S., *Scrip*, April 1994, pp28–32). One advantage that oligosaccharides have over conventional anti-infectives is that they are effective in prevention, as well as treatment, of the infectious disease. In contrast, the use of antibiotics in the prophylaxis of infection may lead to the development of resistance. Moreover, since oligosaccharides do not kill the bacteria, but instead merely inhibit their binding to human tissue, they will not provide any selection pressure for the growth of resistant organisms (Hughes, S., *Scrip*, April 1994, pp28–32).

The synthetic divalent sLex containing polylactosamines of the present invention may be used to treat or prevent infectious diseases. Briefly, a patient diagnosed with such an infection is treated with a composition comprising a divalent sLex, e.g., the sLexLex-saccharide or the sLexLexLex-saccharide. The composition is in a pharmaceutically acceptable excipient at a sufficient dose to block infectious micro-organisms, e.g. bacteria, from binding to the correspondent oligosaccharides on the corresponding, e.g. endothelial, cell surface. The composition is given in a regime such that a serum concentration is achieved in about the nanomolar to micromolar range until the condition is sufficiently ameliorated.

When administered to the patient, the composition is formulated in any manner which makes it suitable for oral, parenteral, nasal, enteric or rectal administration with a pharmaceutically acceptable excipient or vehicles, e.g., isotonic saline, in accordance with conventional pharmaceutical practice. The dosage level of the reagent will be sufficient to provide an anti-infective effect by the blocking of selectin, and especially L-selectin-mediated adhesion events in the patient.

By an "efficacious level" of a composition of the invention is meant a level at which some relief is afforded to the patient who is the recipient of the treatment.

The pharmaceutical compositions of the invention are administered in amounts sufficient to antagonize (fully or partially) the patient's native selectin, and especially L-selectin, binding to biological targets of such selectin in such patient, and specifically to endothelial cells.

Amounts and regimens for the adminstration of selectin-binding carbohydrates and compositions of the invention can be determined readily by those with ordinary skill in the clinical art of treating infectious diseases. Generally, the dosage of the composition of the invention will vary depending upon considerations such as: type of synthetic carbohydrate employed; age; health; medical conditions being treated; kind of concurrent treatment, if any, frequency of treatment and the nature of the effect desired; extent of tissue damage; gender; duration of the symptoms; and, counterindications, if any, and other variables to be adjusted by the individual physician. A desired dosage can be administered in one or more applications to obtain the desired results.

Example 8

Figure 8:
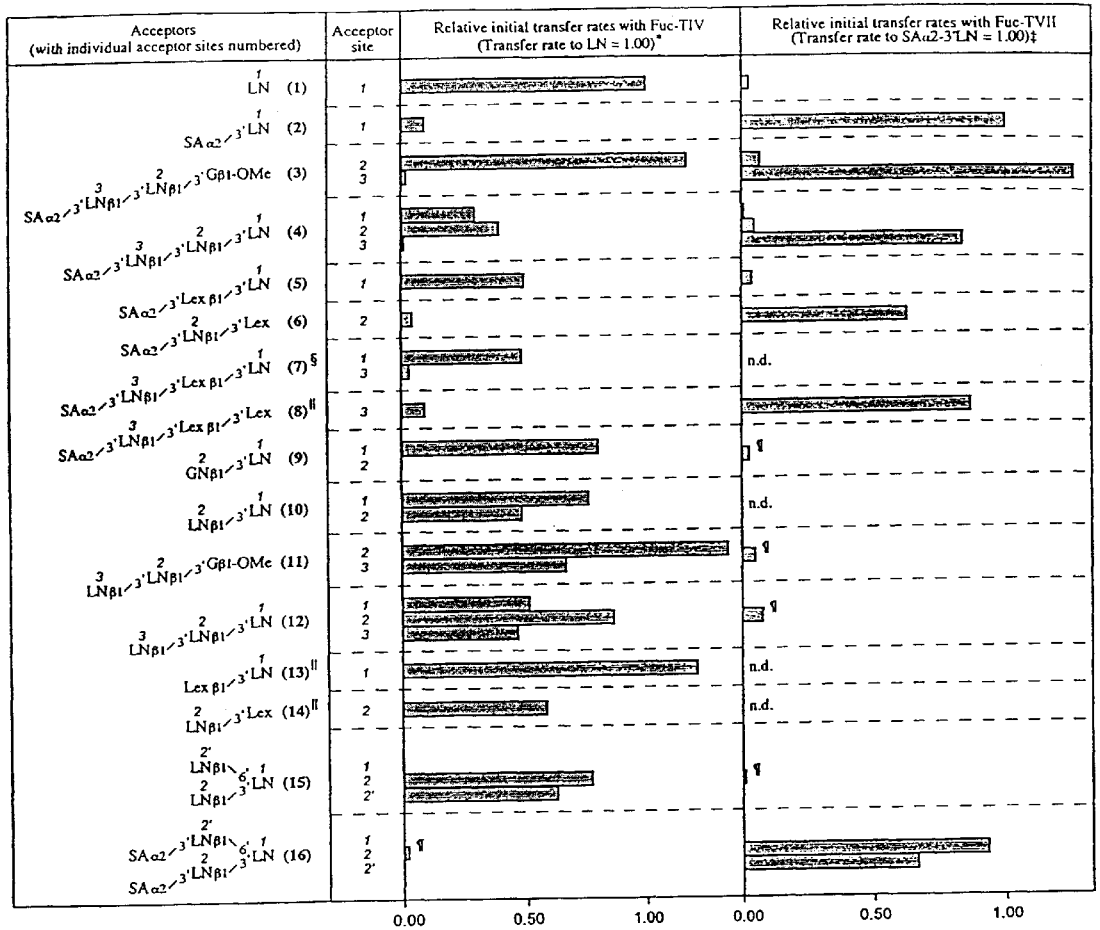
FIG. 8 Relative initial transfer rates at individual acceptor sites of sialylated and neutral polylactosamines, catalyzed by lysates of CHO-cells transfected with human Fuc-TIV and Fuc-TVII. *Transfer rate to LN was typically 3.9 pmol/μg protein/h; ‡Transfer rate to SAα2-3'LN was typically 3.2 pmol/μg protein/h; §Only 0.1 5 mM acceptor was used, the reference acceptor was also 0.15 mM; ‖Only 1 mM acceptor was used, the reference acceptor was also 1 mM. Glycan 8 was analyzed only once; ¶The acceptor site-specificity was not determined; n.d., not determined.

Complementary Acceptor- and Sites-Specificities of Fuc-TIV and Fuc-TVII allow Effective Biosynthesis of Sialyl-triLex and Related Polylactosamines (Bolded Numbering Corresponds to Glycan Structures in FIG. 8)

In the present example, the acceptor- and site-specificies of the two granulocyte α1,3-fucosyltransferases, Fuc-TIV and Fuc-TVII, were characterized.

It was found that Fuc-TIV can transfer fucose efficiently to all N-acetyllactosamine (LN) units in neutral polylactosamines, and to the "inner" LN units of α2,3-sialylated acceptors, but is ineffective in transfer to the distal α2,3-sialyated LN unit in α2,3-sialylated acceptors. Fuc-TVII, by contrast, effectively fucosylates only the distal α2,3-sialylated LN unit in α2,3-sialylated acceptors, and thus exhibits an acceptor site-specificity that is complementary to Fuc-TIV. Furthermore, the consecutive action of Fuc-TIV and Fuc-TVII, in vitro, can convert the long-chain sialoglycan SAα2-3'LNβ1-3'LNβ1-3'LN into the monosialylated, trifucosylated polylactosamine SAα2-3 'Lexβ1-3 'Lexα1-3 'Lex known as sialyl-triLex. The complementary in vitro acceptor site-specificities of Fuc-TIV and Fuc-TVII imply that these enzymes cooperate in vivo in the biosynthesis of monosialylated, multifucosylated polylactosamine components of selectin counterreceptors on human leukocytes.

Transfected Cells and Cell Lysates—The transfection of CHO-cells stably expressing human Fuc-TIV or Fuc-TVII has been described previously (Lowe, J. B., et al., *J. Biol. Chem.* 266:17467–17477 (1991); Natsuka, S., et al., *J. Biol. Chem.* 269:16789–16794 (1994)). For the enzyme assays, the cells were lysed in 1% Triton X-100 on ice in the presence of a mixture of protease inhibitors (16 μg/ml benzamidine HCl, 10 μg/ml phenanthroline, 10 μg/ml aprotinin, 10 μg/ml leupeptin, 10 μg/ml pepstatin A, 1 mM PMSF, Pharmingen, San Diego, Calif.).

Oligosaccharide Acceptors—The structures of the oligosaccharide acceptors are shown in FIG. 8. Glycan 1 was from Sigma (St. Louis, Mo.), and glycan 2 from Oxford Glycosystems (Abingdon, UK). The others were synthesized enzymatically. Briefly, glycan 11 was constructed from GlcNAcβ1-3Galβ1-OMe (Sigma) by β1,4-galactosylation (Brew, K., et al., *Proc. Natl. Acad Sci. USA* 59:491–497 (1968)) followed by β1,3-N-acetylglycosaminylation (Seppo, A., et al., *Biochem. Cell Biol.* 68:44–53 (1990)) and a second round of β1-4-galactosylation. The intermediates as well as the final product were isolated in pure form; $^1$H NMR-spectrum of 11 at 500 MHZ confirmed its structure; MALDI-TOF mass spectrometry (MS) revealed that the sample was pure and had the expected molecular weight, (M+Na)$^+$ m/z 948.0 (calc. 947.9). Glycan 3 was obtained from glycan 11 by α2,3-sialylation as in (Maaheimo, H., et al., *Eur. J. Biochem.* 234:616–625 (1995)). Glycan 12 was constructed from the GNβ1-3 'LNβ1-3 'LN (Leppänen, A., et al., *Biochemistry* 30:9287–9296(1991)) by β1,4-galactosylation, MALDI-TOF MS: (M+Na)$^+$ m/z 1137.1 (calc. 1137.0). Glycan 4 was obtained by glycan 12 by α2,3-sialylation. Glycan 15 was synthesized as in (Renkonen, O., et al., *Biochem. Cell. Biol.* 68:1032–1036 (1990)), MALDI-TOF MS: (M+Na)$^+$ m/z 1136.9 (calc. 1137.0). Glycan 16 was obtained by a 2,3-salylation of 15. In the synthesis of glycan 8, GNβ1-3'LNβ1-3'LN was α1,3 [$^{14}$C]fucosylated at both LN units with α1,3/4-FucTs ofhuman milk and then β1,4-galactosylated. MALDI-TOF MS of the resulting octasaccharide LN β1-3'Lexβ1-3'Lex gave (M+Na)$^+$ m/z 1429.3 (calc. 1429.3). The octasaccharide was finally α2,3-sialylated to give glycan 8. Degradation of glycan 8 by sialidase and a mixture of β-galactosidase and β-N-acetylhexosaminidase gave the neutral hexasaccharide [$^{14}$C]Fucα1-3LNβ1-3'[$^{14}$C]Fucα1-3LN, which chromatographed like an authentic marker on paper. In the synthesis of glycan 5, glycan 10 was converted to the pentasaccharide LNβ1-3'(GNβ1-6')LN as in (Niemelä, R., et al., *Carbohydr. Res.* 279:331–338 (1995); Maaheimo, H., et al., *Carbohydr. Res.* 297:53–59 (1997)), MALDI-TOF MS: (M+Na)$^+$ m/z 974.8 (calc. 974.9). The product was α2,3-sialylated, α1,3-fucosylated selectively at the distal, sialylated LN-unit (Niemelä, R., et al., *Carbohydr. Res.* 279:331–338 (1995), and treated with β-N-acetylhexosaminidase for removal of the protecting β1-6GN-unit to give glycan 5. Glycan 6, in turn, was obtained by α1,3-fucosylating glycan 9 at the LN unit by human milk α1,3/4-Fuc-Ts. The product was then β1,4-galactosylated and finally α2,3-sialylated. Glycan 7 was synthesized by α2,3-sialylation of the heptasaccharide LNβ1-3'Lexβ1-3'LN, prepared by β1,4-galactosylation of GNβ1-3'Lexβ1-3'LN, which had been isolated from a mixture of monofucosylated isomers by wheat germ agglutinin (WGA)-agarose chromatography. LNβ1-3'Lexβ1-3'N was characterized by $^1$H-NMR-spectroscopy, MALDI-TOF MS: (M+Na)$^+$ m/z 1282.5 (calc. 1282.5). Glycan 9 was obtained by β1,3-N-acetylglucosaminylation of LN (Seppo, A., et al., *Biochem. Cell Biol.* 68:44–53 (1990)), MALDI-TOF MS: (M+Na)$^+$ m/z 609.7 (calc. 609.5). Glycan 10 was synthesized by β1,4-galactosylation of glycan 9. Glycans 13 and 14 were obtained by separating monofucosylated derivatives of glycan 10 by WGA chromatography. Glycan 13, MALDI-TOF MS: (M+Na)$^+$ m/z 917.9 (calc. 917.8). Glycan 14, MALDI-TOF MS: (M+Na)$^+$ m/z 917.8 (calc. 917.8).

Fucosyltransferase Reactions—GDP-[$^{14}$C]Fucose (100,000 cpm, Amersham, UK), GDP-fucose (1 nmol, Sigma) and the individual polylactosamine acceptors (50 nmol) were incubated for 1 h at 37° C. in 10 μl of 50 mM MOPS, pH 7.2, containing 10 mM MnCl$_2$, 10 mM fucose, 5 mM ATP, 0.4% TX- 100 and lysates of CHO-cells transected with Fuc-TIV or Fuc-TVII (35–50 μg protein, assayed by the BCA kit of Pierce, Rockford, Ill.). 100 nmol LN and 100 nmol Saα2–3LN were used as reference acceptors. The reactions were terminated by adding 10 μl ethanol followed by 100 μl of ice cold water, and the reaction mixtures containing acidic glycans were purified by gel filtration on a Superdex column, subsequently fractionated by anion exchange chromatography on a MonoQ column and finally desalted on a Superdex column. The reaction mixtures obtained from neutral acceptors were desalted in a mixed bed ion exchange resin, after which the mixtures of acceptor and product were isolated by gel filtration. In all cases, the reaction products were quantitated by subjecting aliquots of the purified mixture of unlabeled surplus acceptor and labeled product to liquid scintillation counting. All reactions were run and analyzed twice.

Methods used in the Analysis of Fuc-TIV- and FUC-TVII-reactions

Degradations with a mixturej ack bean β-galactosidase (EC 3.2.1.23, Sigma), jack bean β-N-acetylhexosaminidase (EC 3.2.1.30, Sigma) (Niemelä, R., et al., *Glycoconjugate J.* 12:36–44 (1995)), *A. ureafaciens* sialidase (EC 3.2.1.18, Boehringer, Mannheim, Germany (Seppo, A., et al, *Glycobiology* 6:65–71 (1996)) and *B. fragilis* endo-βgalactosidase (EC 3.2.1.103, Boehringer) (acetylglucosaminylation (Leppänen, A., et al., *Biochemistry* 30:9287–9296 (1991)) were carried out as previously described.

Gel filtration was performed in a column of Superdex Peptide HR 10/30 (Pharmacia, Sweden), with 50 mM NH$_4$HCO$_3$ as the eluant at a flow rate of 1 ml/min. The eluant was monitored at 205 or 214 nm, and oligosaccharides were quantified against external GN and SA. Neutral oligosaccharides were desalted by filtration in water through AG-50W (H$^+$) and AG-1 (AcO$^-$) (Bio-Rad, CA).

Paper chromatography of radiolabeled oligosaccharides was carried out as in (Renkonen, O., et al., *Glycoconjugate J.* 6:129–140 (1989)), using the upper phase of n-butanol:acetic acid:water (4:1:5) (v/v) (Solvent A) for the chromatographic runs and Optiscint (Wallac, Finland) for the liquid scintillation counting. Anion exchange chromatography on a Mono Q (5/5) column (Pharmacia) was performed essentially as in (Maaheimo, H., et al., *Eur. J. Biochem.* 234:616–625 (1995)).

Oligosaccharide Markers—The hexassacharide Lexβ1-3'Lex and the nonasaccharide Lexβ1-3'Lexβ1-3'Lex, MALDI-TOF MS: (M+Na)$^+$ m/z 1575.8 (calc. 1575.5) as well as the mixture of the octasaccharide Lexβ1-3'Lexβ1-3'LN and its isomers, MALDI-TOF MS: (M+Na)$^+$ m/z 1429.5 (calc. 1429.3) were synthesized from fucose-free precursors in the presence of GDP-fucose and purified α1,3-fucosyltransferase (Seppo, A., et al., *Glycobiology* 6:65–71 (1996)).

Fuc-TIV and Fuc-TVII Exhibit Shared and Distinct Acceptor Substrate Specifities. A panel of neutral and sialylated polylactosamine acceptors was synthesized, and individual acceptor substrates were utilized in in vitro fucosyltransferase assays containing radiolabeled GDP-fucose and CHO-transfectant-derived recombinant human Fuc-TIV or Fuc-TVII. N-acetyllactosamine (LN); glycan 1) and sialyl N-acetyllactosarnine (SAα2-3 'LN; glycan 2) served as reference acceptors for Fuc-TIV and FUC-TVII-dependent reactions, respectively. Fuc-TIV rapidly fucosylates LN (glycan 1), but is ineffective in its ability to fucosylate the sialylated acceptors 2, 6, and 8, each of which can be fucosylated only at the distal, sialylated LN unit (FIG. 8). By contrast, Fuc-TVII effectively fucosylates all sialopolylactosamines tested, except glycan 5, which can be fucosylated only on an internal LN unit (FIG. 8). The neutral glycans 9–15 are efficiently fucosylated by Fuc-TIV, but are poor acceptors when tested with Fuc-TVII. Fuc-TIV also efficiently fucosylates the sialylated linear acceptors 3 and 4, each of which contain "inner" N-acetyllactosamine residues. Furthermore, Fuc-TIV effectively utilizes sialylated, fucosylated linear acceptors 5 and 7, each of which also contain unoccupied "inner" N-acetyllactosamine residues.

Figure 9:
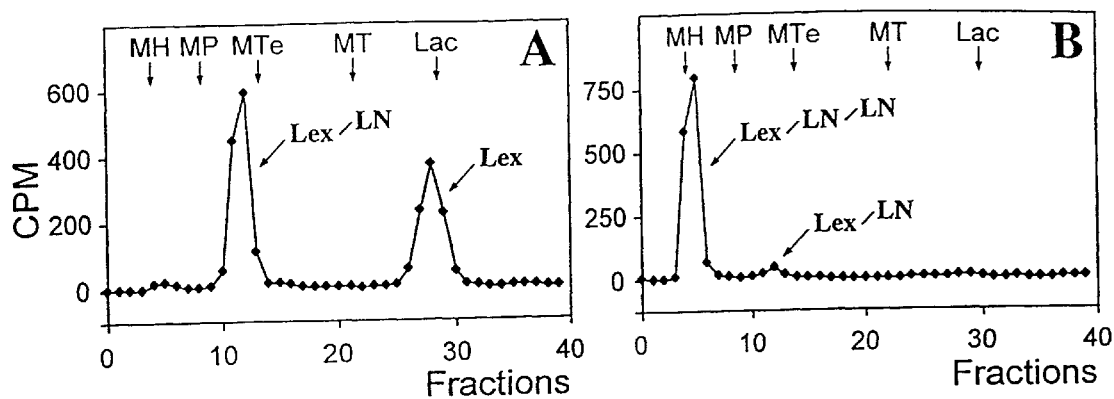
FIG. 9 (Panels A–B) Paper chromatography of oligosaccharides generated by atreatment with sialidase and a mixture of jack bean β-galactosidase and β-N-acetylhexosaminidase from Fuc-TIV-and Fuc-TVII-products of sialoglycan 4. (Panel A) The digest of Fuc-TIV products. (Panel B) The digest of Fuc-TVII products. For both runs: Solvent A, 97 h. Markers: MH, maltoheptaose; MP, maltopentaose; MTe, maltotetraose; MT, maltotriose; Lac, lactose.

Fuc-TIV and Fuc- TVII Show Alternative Site-Specificities on Sialylated Multi-Site Acceptors. To determine which of the different GlcNAc residues were fucosylated in the sialylated multi-site acceptors 3 and 4, the products were degraded by sialidase and then by mixed β-galactosidase and β-N-acetylhexosaminidase. Fuc-TIV transfers rapidly to sialoglycan 4, at both "inner" LN units (residues 1 and 2 in FIG. 8), but transfers to the sialylated LN unit (residue 3) at a rate 30–40 times slower (FIGS. 8 and 9A). In contrast, Fuc-TVII transfers preferentially to the sialylated, distal LN residue of acceptor 4 (FIG. 9B); the rate of transfer to the middle LN unit (residue 2), and to the reducing end LN unit (residue 1) were, respectively, 17 and 84 times slower than transfer to the sialylated LN residue (FIG. 8). The fucosylated products of sialoglycan 3 were analyzed in a similar way to ascertain site-specificity of fucosylation. These analyses indicate that Fuc-TIV overwhelmingly fucosylates at the "inner" LN unit, whereas Fuc-TVII fucosylates preferentially at the distal, sialylated LN unit. Taken together, these results imply that "internal" fucosylation events occurring within sialoglycans are catalyzed by Fuc-TIV, whereas the terminal fucosylation event that creates sialyl Lewis x (sLex) type products is catalyzed by Fuc-TVII.

Figure 10:
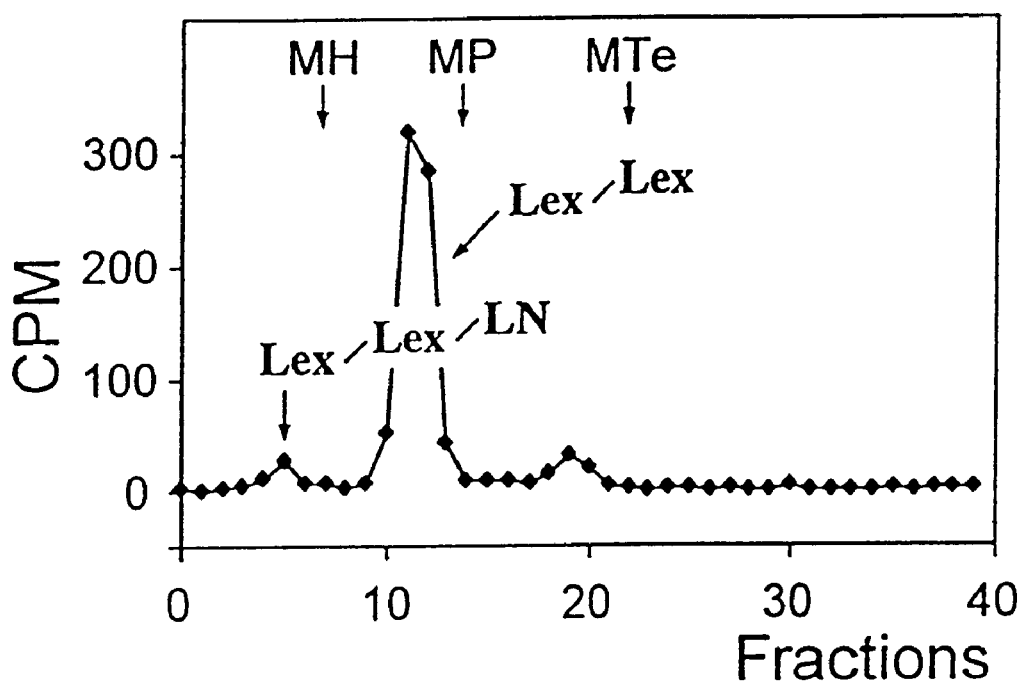
FIG. 10 Paper chromatography of oligosaccharides generated by a treatment with sialidase and a mixture of jack bean β-galactosidase and β-N-acetylhexosaminidase from Fuc-TIV-products of sialoglycan 7. The major peak at fractions 11–12 co-chromatographed with an authentic sample of the hexasaccharide Lexp 1-3 'Lex. The small peak at fraction 5 chromatographed like Lexβ1-3' Lexβ1-3'LN and its isomers. Solvent A, 168 h; markers as in FIG. 9.

Fuc-TIV and Fuc-TVII Show Alternative Preference Among Pre-Fucosylated Acceptors of the VIM-2- and sLex-type. In vitro assays using the pre-fucosylated glycans 5 and 6 indicate that Fuc-TIV transfers fucose to the "inner" LN unit, and that Fuc-TVII transfers to the sialylated, distal LN unit (FIG. 8). Hence, the two enzymes complement each other efficiently in the synthesis of the sialylated, bi-fucosylated epitope from the fucose-free precursor via intermediates of VIM-2 and sLex type glycans. The unlabeled glycan SAα2-3'LNβ1-3'Lexβ1-3'LN (glycan 7) was then used as an acceptor in a Fuc-TIV-dependent reaction. Structural characterization of the products (FIG. 10) revealed that 86% of the [$^{14}$C] fucose were transferred to the "innermost" LN unit (residue 1), generating SAα2-3'LNβ1-3Lex β1-3'[$^{14}$C]Lex (glycan 8). Less than 5% of the fucose transfer occurred at the sialylated LN unit (residue 3). These observations, together with those displayed in FIG. 9A demonstrate that Fuc-TIV can convert glycan 4 into the bifucosylated glycan 8.

Figure 11:
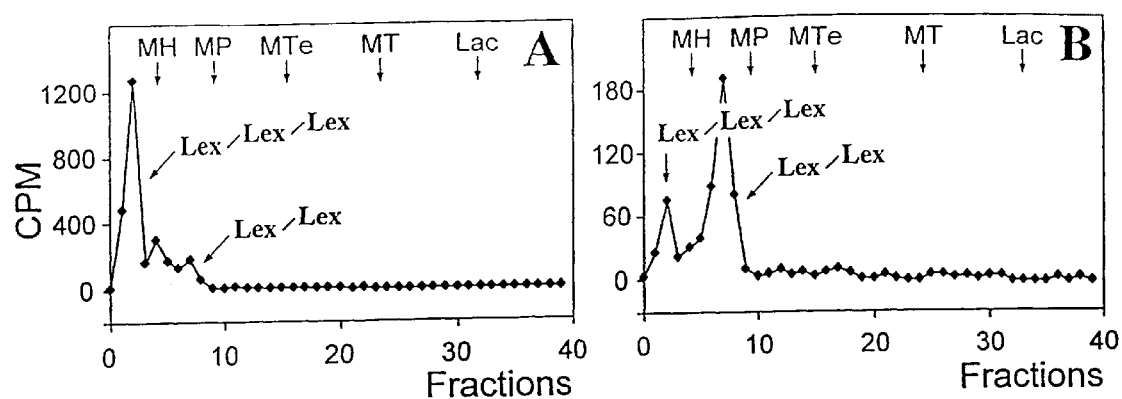
FIG. 11. (Panels A–B) Paper chromatography of oligosaccharides generated by atreatment with sialidase and amixture of jack bean β-galactosidase and β-N-acetylhexosaminidase from Fuc-TVII- and Fuc-TIV-products of sialoglycan 8. (Panel A) The digest of Fuc-TVII products. The major peak at fraction 2 co-chromatographed with an authentic sample of the nonasaccharide [$^{14}$C]Lexβ1-3[$^{14}$C]Lexβ1-3'[$^{14}$C]Lex. For comparison, the digest from the original sialoglycan 8 revealed only the peak of the hexasaccharide [$^{14}$C]Lexβ1-3'[$^{14}$C]Lex at fraction 7. (Panel B) The digest of Fuc-TIV products. The small peak at fraction 2 represents [$^{14}$C]Lexβ1-3'[$^{14}$C]Lexβ1-3'[$^{14}$C]Lex, derived from the trifucosylated sialoglycan product, while the peak at fraction 7 is [$^{14}$C]Lexβ1-3[$^{14}$C]Lex, that was derived from the radiolabeled acceptor (8) by the exohydrolase treatment. For both runs: Solvent A, 120 h; markers as in FIG. 9.

Fuc-TVII Catalyzes Rapid Fucosylation of the Monosialyl-Bifucosyl Glycan 8, at the Distal, Sialylated LN Unit. Fuc-TVII was found to fucosylate glycan 8 nearly as rapidly as glycan 2 (FIG. 8), to yield as a major product SAα2-3'[$^{14}$C]Lexβ1-3'Lexβ1-3'Lex (FIG. 11A). Fuc-TIV was found to be competent to construct the identical product, but only at a rate that represents 6–7% of the rate catalyzed by Fuc-TVII (FIG. 11B). The efficient conversion of glycan 4 to glycan 8 in two steps catalyzed by Fuc-TIV, but not by Fuc-TVII, and the further rapid Fuc-TVII-dependent conversion of glycan 8 to SAα2-3'Lexβ1-3'Lexα1-3 'Lex, demonstrate that the monosialylated, fucose-free tri-lactosamine claim (4) is converted into the sialyl-triLex product by the complementary actions of the two α1, 3-fucosyltransferases present in human leukocytes.

Figure 12:
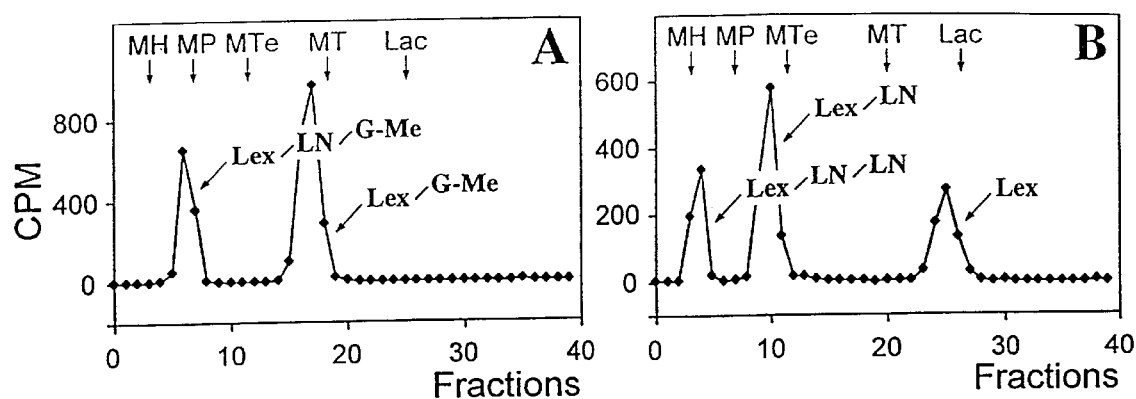
FIG. 12. (Panels A–B) Paper chromatography of oligosaccharides generated by a treatment with a mixture of jack bean β-galactosidase and β-N-acetylhexosaminidase from Fuc-TIV-products of neutral glycans. (Panel A) Exoglycosidase digest from the products of glycan 11. (Panel B) Exoglycosidase digest from the products of glycan 12. For both runs: Solvent A, 99 h; markers as in FIG. 9.
Figure 13:
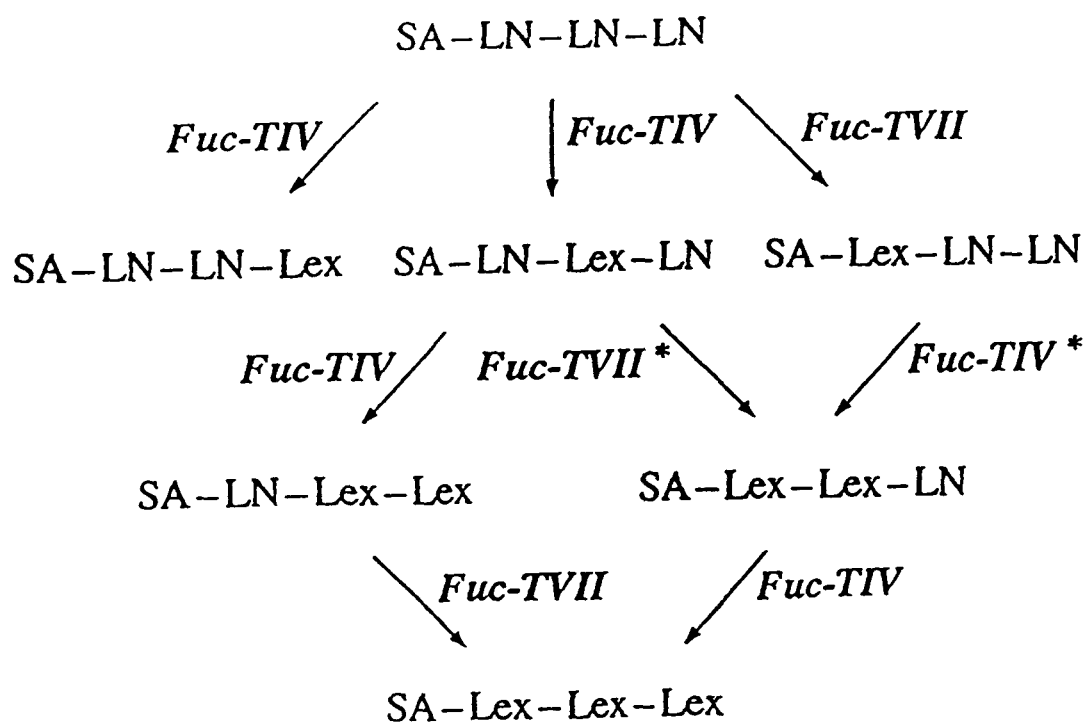
FIG. 13. Biosynthetic pathways leading to multiple fucosylation of a mono sialylated, fuco se-free polylactosamine that has a long chain. The scheme shows the complementary Fuc-TIV- and Fuc-TVII-reactions traced by the present experiments. *These reactions were actually demonstrated by using sialofucoglycans from which the reducing end LN unit was missing.

Site-Specificity of Fuc-TIV Reactions with Neutral Linear Acceptors. Fuc-TIV efficiently fucosylated GNP 1-3 'LN (9), representing a growing lactosamine chain (FIG. 8), whereas Fuc-TVII did not utilize this acceptor. Fucosylation occurred only at the reducing end N-acetylglucosamine moiety, as the [$^{14}$C]-fuicosylated product was cleaved by β-N-acetylhexosaminidase to [$^{14}$C]Lex (data not shown). Fuc-TIV also transferred efficiently to LNβ1-3 'LNβ1-3'Galβ1-OMe (glycan 11), most rapidly (67%) to the middle LN unit (residue 2 in FIG. 8) and more slowly (33%) to the terminal LN unit (FIG. 12A). When the hexassacharide LN1-3'LN1-3'LN (glycan 12) was used with Fuc-TIV, 28% of the initial fucosylation occurred at the reducing end LN unit, 47% occurred at the middle LN unit, and 25% occurred at the non-reducing end LN unit (FIG. 12B). Fuc-TIV also transferred rapidly to the pre-fucosylated glycans Lexβ1-3 'LN (glycan 13) and LNβ1-3'Lex (glycan 14), confirming that fucosylation of vicinal LN units is feasible.

All references mentioned herein are incorporated by reference in the disclosure.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

What is claimed is:

1. A synthetic oligosaccharide having the formula:

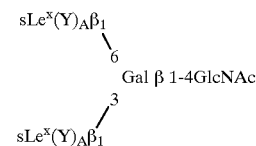

wherein

Gal is galactose;

GlcNAc is N-acetylglucosamine;

Y is Galβ1-4GlcNAc or Galβ1-4(Fucα1-3)GlcNAc, wherein Fuc is fucose sLe$^x$ is NeuNAcα2-3Galβ1-4 (Fucα1-3)GlcNAc, wherein NeuNAc is sialic acid; and A is ≧1.

2. The synthetic oligosaccharide of claim 1 which has the formula:

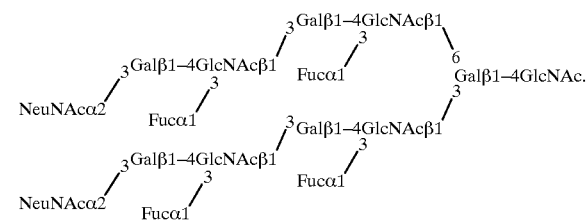

3. The synthetic oligosaccharide of claim 1 which has the formula:

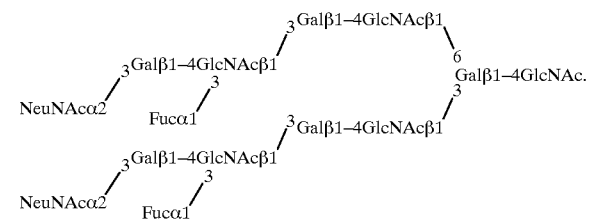

4. The synthetic oligosaccharide of claim 1 which has the formula:

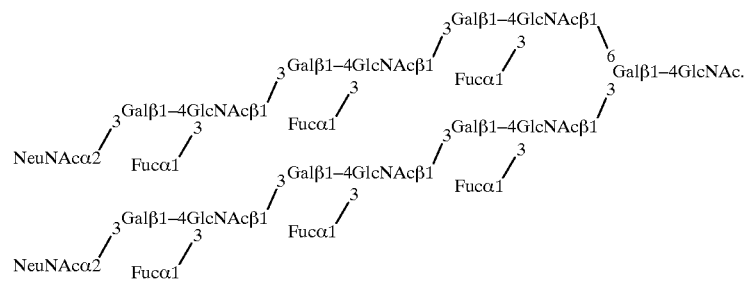

5. The synthetic oligosaccharide of claim 1 which has the formula:
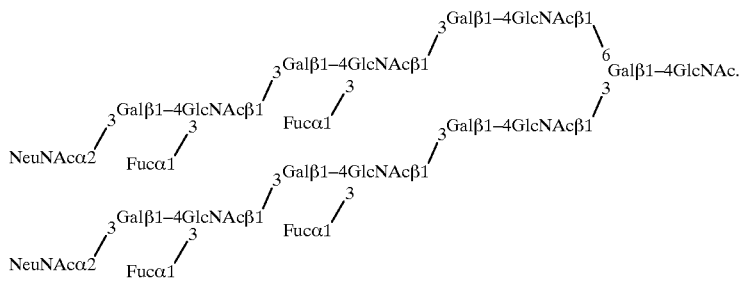
6. The synthetic oligosaccharide of claim 1 which has the formula:
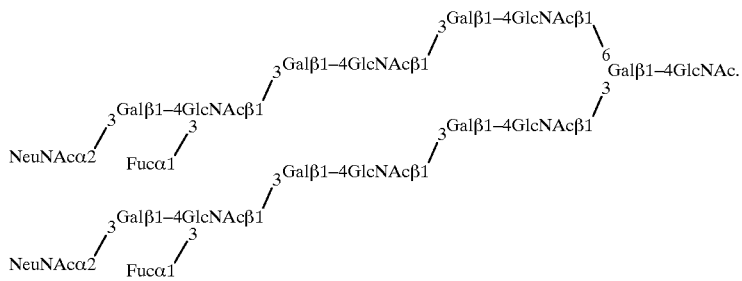
7. A pharmaceutical composition comprising the synthetic oligosaccharide of any one of claims 1–6 in a pharmaceutically acceptable carrier.
* * * * *